(12) United States Patent
Metcalf

(10) Patent No.: US 10,610,805 B1
(45) Date of Patent: Apr. 7, 2020

(54) METHODS TO SEPARATE CANNABIDIOL AND TETRAHYDROCANNABINOL

(71) Applicant: Natural Extraction Systems, LLC, Boulder, CO (US)

(72) Inventor: Douglas G. Metcalf, Erie, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 0 days.

(21) Appl. No.: 16/680,365

(22) Filed: Nov. 11, 2019

Related U.S. Application Data

(60) Provisional application No. 62/777,608, filed on Dec. 10, 2018, provisional application No. 62/780,181, filed on Dec. 14, 2018, provisional application No. 62/787,724, filed on Jan. 2, 2019, provisional application No. 62/803,412, filed on Feb. 8, 2019, provisional application No. 62/812,852, filed on Mar. 1, 2019, provisional application No. 62/818,695, filed on Mar. 14, 2019, provisional application No. 62/821,971, filed on Mar. 21, 2019, provisional application No. 62/832,009, filed on Apr. 10, 2019, provisional application No. 62/839,569, filed on Apr. 26, 2019, provisional application No. 62/860,218, filed on Jun. 11, 2019, provisional application No. 62/925,203, filed on Oct. 23, 2019, provisional application No. 62/933,742, filed on Nov. 11, 2019.

(51) Int. Cl.
*C07C 29/84* (2006.01)
*C07D 311/00* (2006.01)
*B01D 11/00* (2006.01)
*B01D 11/04* (2006.01)
*C07D 311/80* (2006.01)

(52) U.S. Cl.
CPC .......... *B01D 11/0492* (2013.01); *C07C 29/84* (2013.01); *C07D 311/80* (2013.01)

(58) Field of Classification Search
CPC ........ C07C 29/84; C07D 311/20; B01D 11/00
See application file for complete search history.

(56) References Cited

U.S. PATENT DOCUMENTS

2018/0360757 A1\* 12/2018 Doroudian ........... A61K 31/047

FOREIGN PATENT DOCUMENTS

EP 3459536 A1 \* 3/2019 ............. A61K 31/05

\* cited by examiner

*Primary Examiner* — Sikarl A Witherspoon
(74) *Attorney, Agent, or Firm* — Cooley LLP

(57) ABSTRACT

Various aspects of this patent document relate to methods to separate cannabidiol and tetrahydrocannabinol by adjusting their solubility in alcohol and water solutions.

20 Claims, 1 Drawing Sheet

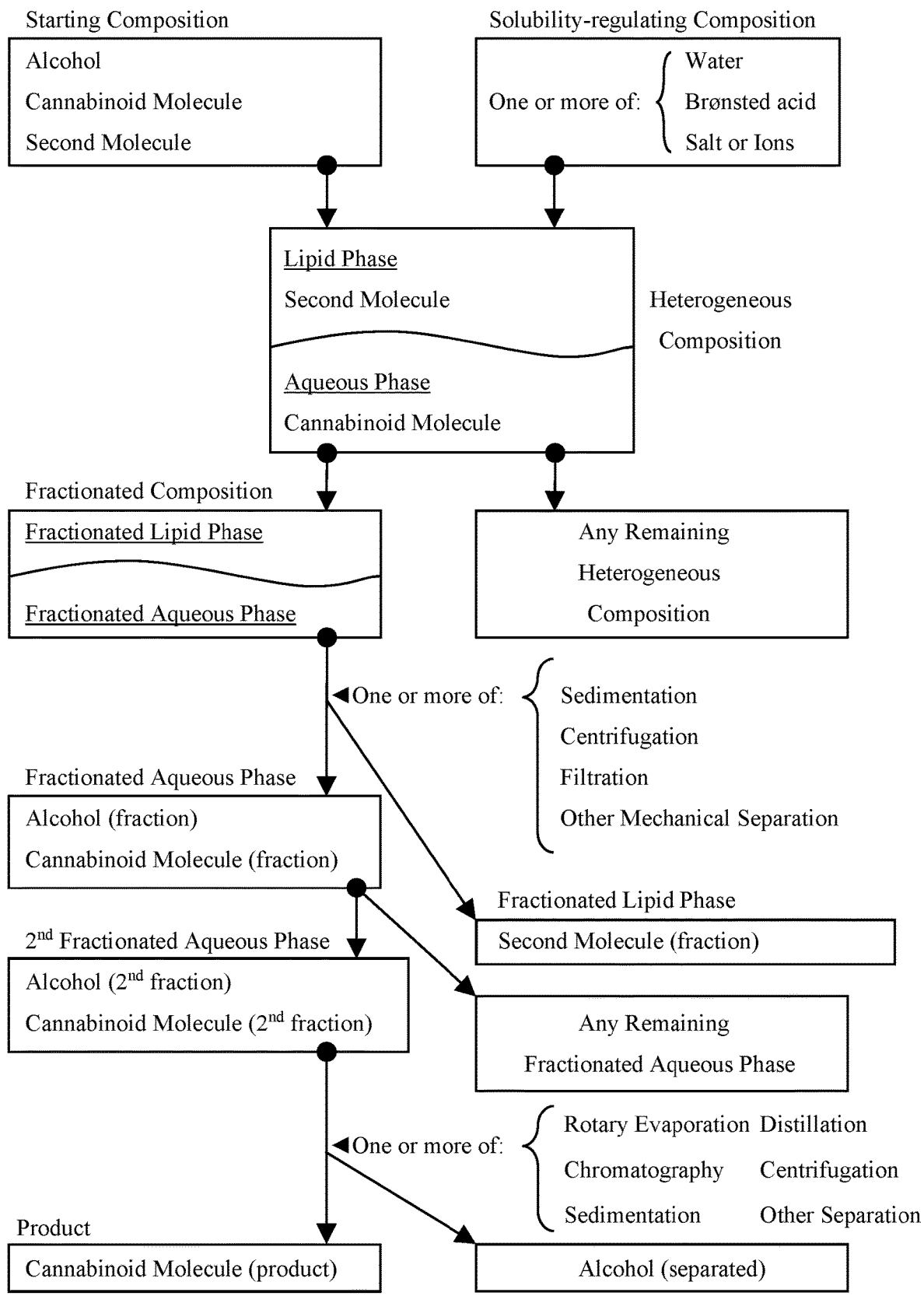

METHODS TO SEPARATE CANNABIDIOL AND TETRAHYDROCANNABINOL

RELATED PATENT APPLICATIONS

This patent application claims the benefit under 35 U.S.C. § 120 of the following prior-filed United States provisional patent applications: U.S. 62/777,608, filed Dec. 10, 2018; U.S. 62/780,181, filed Dec. 14, 2018; U.S. 62/787,724, filed Jan. 2, 2019; U.S. 62/803,412, filed Feb. 8, 2019; U.S. 62/812,852, filed Mar. 1, 2019; U.S. 62/818,695, filed Mar. 14, 2019; U.S. 62/821,971, filed Mar. 21, 2019; U.S. 62/832,009, filed Apr. 10, 2019; U.S. 62/839,569, filed Apr. 26, 2019; U.S. 62/860,218, filed Jun. 11, 2019; U.S. 62/925,203, filed Oct. 23, 2019; and U.S. 62/933,742, filed Nov. 11, 2019, and the contents of each prior-filed application is incorporated by reference in its entirety.

BACKGROUND

Concentrated cannabinoid products are typically produced by extracting lipids from *cannabis*, decarboxylating the cannabinoid carboxylic acids of an extract, and then purifying the decarboxylated cannabinoids. Industrial hemp extracts contain both cannabidiol, which displays significant beneficial pharmacological properties, and tetrahydrocannabinol, which is a regulated psychoactive drug. State-of-the-art techniques to separate cannabidiol from tetrahydrocannabinol to reduce the tetrahydrocannabinol content of a cannabidiol product include flash chromatography, high-performance liquid chromatography, centrifugal partition chromatography, and crystallization. These methods generally require hydrocarbon solvents, however, which are both expensive and limit the ability to obtain organic certification on finished consumer products. Separation methods that reduce the need for hydrocarbon solvents and allow organic certification therefore remain desirable.

SUMMARY

Various aspects of this patent document relate to methods to separate a cannabinoid molecule from a second molecule based on solubility. The disclosed methods generally involve adjusting the solubility of either the cannabinoid molecule or the second molecule in a liquid to produce a heterogeneous composition comprising an aqueous phase, which contains a majority of one molecule, and a lipid phase, which contains a majority of the other molecule. The aqueous phase is then separated from the lipid phase to separate the cannabinoid molecule and the second molecule. The solubility of the cannabinoid molecule or the second molecule can be adjusted by one or more of (i) adjusting the hydrophilicity of the liquid (for example, by increasing the water concentration of the liquid); (ii) adjusting the hydrogen cation concentration of the liquid (for example, by adding a Brønsted acid to the liquid); (iii) adjusting the ionic strength of the liquid (for example, by adding a salt to the liquid); (iv) adjusting the temperature of the liquid (for example, by decreasing the temperature of the liquid); or (v) adjusting the pressure of the liquid (for example, by increasing the pressure of the liquid). When organic ethanol is used as the solvent of the liquid, then the methods set forth in this patent document are generally amenable to organic certification.

BRIEF DESCRIPTION OF THE DRAWING

The FIGURE is a flow chart that depicts an embodiment of this patent document to provide a graphical representation to aid the interpretation of this patent document. The FIGURE shall not be construed to limit either the disclosure of this patent document or any patent claim that matures from this patent document.

DETAILED DESCRIPTION

Various aspects of this patent document relate to methods to separate a cannabinoid from a second molecule. Representative cannabinoids include cannabidiol, cannabidivarin, tetrahydrocannabinol, tetrahydrocannabivarin, cannabigerol, cannabichromene, and cannabinol. Each cannabinoid can exist in an aqueous solution either as a neutrally-charged molecular cannabinoid, which is strongly favored at neutral pH, or as a negatively-charged ionic cannabinoid that is a phenolate, which can be favored at a pH above 8 depending on the nature of the solvent and any cosolvent. As used in this patent document, a cannabinoid that lacks the modifier "molecular" or "ionic" refers to (1) the combined molecular and ionic forms of the cannabinoid provided that the cannabinoid is dissolved in a protic solvent such as an alcohol or water, or (2) the molecular cannabinoid provided that both (a) the cannabinoid is present in either an oil or a solid and (b) context does not otherwise indicate that the cannabinoid is a salt. Various cannabinoids are depicted in Formulas I, II, III, IV, V, VI, VII, VIII, IX, X, XI, XII, XIII, XIV, XV, and XVI, and the chemical names of these cannabinoids are set forth in Table 1.

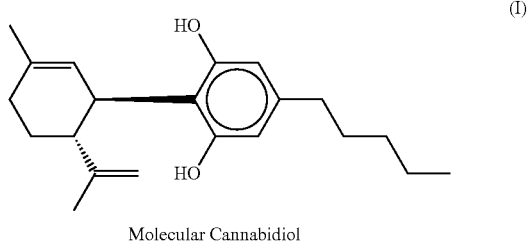

Molecular Cannabidiol (I)

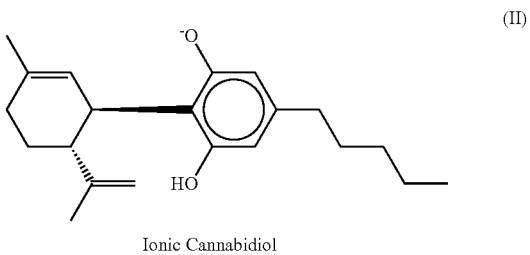

Ionic Cannabidiol (II)

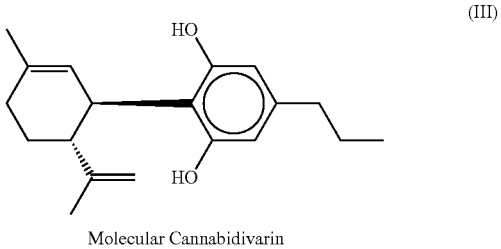

Molecular Cannabidivarin (III)

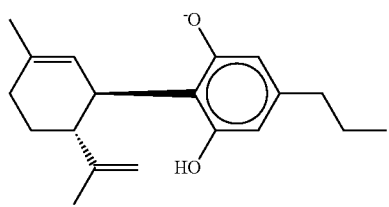

Ionic Cannabidivarin (IV)

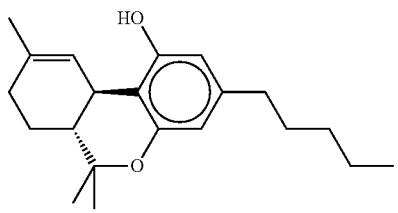

Molecular Tetrahydrocannabinol (V)

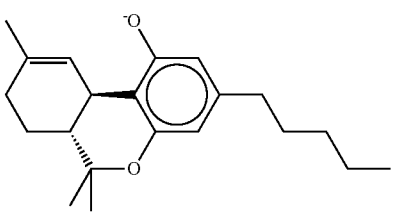

Ionic Tetrahydrocannabinol (VI)

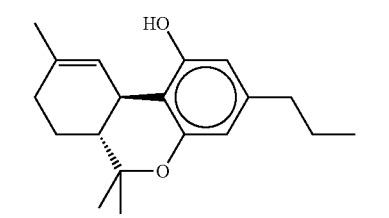

Molecular Tetrahydrocannabivarin (VII)

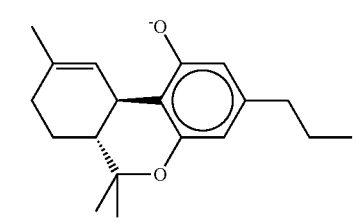

Ionic Tetrahydrocannabivarin (VIII)

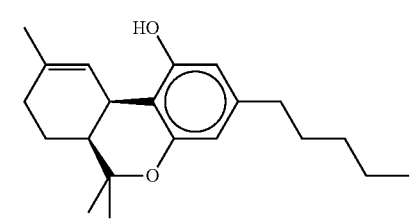

Molecular (6aS,10aR) Stereoisomer of Tetrahydrocannabinol (IX)

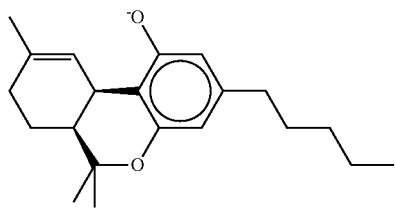

Ionic (6aS,10aR) Stereoisomer of Tetrahydrocannabinol (X)

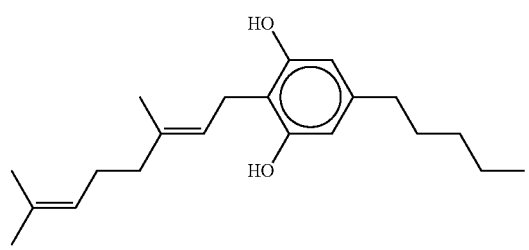

Molecular Cannabigerol (XI)

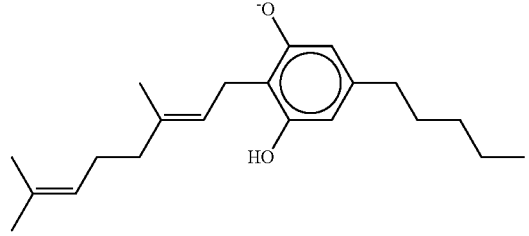

Ionic Cannabigerol (XII)

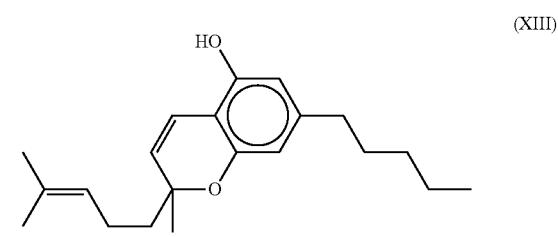

Molecular Cannabichromene (XIII)

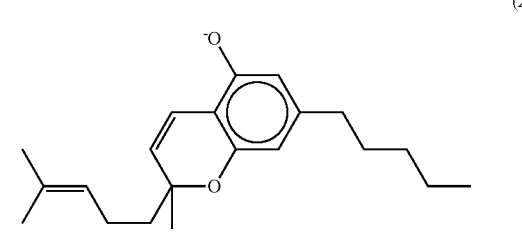

Ionic Cannabichromene (XIV)

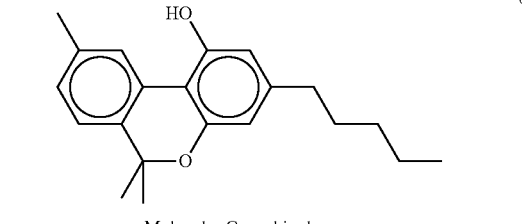

Molecular Cannabinol (XV)

-continued

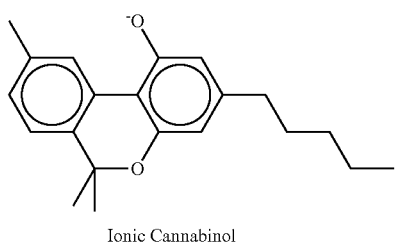

Ionic Cannabinol (XVI)

TABLE 1

Names of the Cannabinoids of Formulas I-XVI

| Formula | Common Name | Chemical Name |
|---|---|---|
| I | Molecular Cannabidiol | 2-[(1R,6R)-6-isopropenyl-3-methylcyclohex-2-en-1-yl]-5-pentylbenzene-1,3-diol |
| II | Ionic Cannabidiol | 2-[(1R,6R)-6-isopropenyl-3-methylcyclohex-2-en-1-yl]-3-hydroxy-5-pentylphenolate |
| III | Molecular Cannabidivarin | 2-[(1R,6R)-6-isopropenyl-3-methylcyclohex-2-en-1-yl]-5-propylbenzene-1,3-diol |
| IV | Ionic Cannabidivarin | 2-[(1R,6R)-6-isopropenyl-3-methylcyclohex-2-en-1-yl]-3-hydroxy-5-propylphenolate |
| V | Molecular Tetrahydrocannabinol | (6aR,10aR)-6,6,9-trimethyl-3-pentyl-6a,7,8,10a-tetrahydro-6H-benzo[c]chromen-1-ol |
| VI | Ionic Tetrahydrocannabinol | (6aR,10aR)-6,6,9-trimethyl-3-pentyl-6a,7,8,10a-tetrahydro-6H-benzo[c]chromen-1-oxide |
| VII | Molecular Tetrahydrocannabivarin | (6aR,10aR)-6,6,9-trimethyl-3-propyl-6a,7,8,10a-tetrahydro-6H-benzo[c]chromen-1-ol |
| VIII | Ionic Tetrahydrocannabivarin | (6aR,10aR)-6,6,9-trimethyl-3-propyl-6a,7,8,10a-tetrahydro-6H-benzo[c]chromen-1-oxide |
| IX | (6aS,10aR) Isomer of Tetrahydrocannabinol | (6aS,10aR)-6,6,9-trimethyl-3-pentyl-6a,7,8,10a-tetrahydro-6H-benzo[c]chromen-1-ol |
| X | Ionic (6aS,10aR) Isomer of Tetrahydrocannabinol | (6aS,10aR)-6,6,9-trimethyl-3-pentyl-6a,7,8,10a-tetrahydro-6H-benzo[c]chromen-1-oxide |
| XI | Molecular Cannabigerol | 2-[3,7-dimethylocta-2,6-diene-1-yl]-5-pentylbenzene-1,3-diol |
| XII | Ionic Cannabigerol | 2-[3,7-dimethylocta-2,6-diene-1-yl]-3-hydroxy-5-pentylphenolate |
| XIII | Molecular Cannabichromene | 2-methyl-2-(4-methylpent-3-en-1-yl)-5-hydroxy-7-pentyl-2H-1-benzopyran |
| XIV | Ionic Cannabichromene | 2-methyl-2-(4-methylpent-3-en-1-yl)-7-pentyl-2H-1-benzopyran-5-oxide |
| XV | Molecular Cannabinol | 6,6,9-trimethyl-3-pentyl-6H-benzo[c]chromen-1-ol |
| XVI | Ionic Cannabinol | 6,6,9-trimethyl-3-pentyl-6H-benzo[c]chromen-1-oxide |

Various aspects of the disclosure relate to a method to separate a cannabinoid molecule from a second molecule. In some embodiments, the second molecule is also a cannabinoid molecule.

In some embodiments, the cannabinoid molecule is selected from cannabidiol, cannabidivarin, cannabigerol, and cannabigerovarin (CBGV; 2-[3,7-dimethylocta-2,6-diene-1-yl]-5-propylbenzene-1,3-diol). In some specific embodiments, the cannabinoid molecule is cannabidiol.

In some embodiments, the second molecule is a cannabinoid. In some specific embodiments, the second molecule is a cannabinoid, and the cannabinoid is selected from tetrahydrocannabinol, tetrahydrocannabivarin, (6aS,10aR) isomer of tetrahydrocannabinol, cannabichromene, cannabichromevarin (CBCV; 2-methyl-2-(4-methylpent-3-en-1-yl)-5-hydroxy-7-propyl-2H-1-benzopyran), cannabinol, and cannabivarin (CBNV; 6,6,9-trimethyl-3-propyl-6H-benzo[c]chromen-1-ol). In some very specific embodiments, the second molecule is a cannabinoid, and the cannabinoid is tetrahydrocannabinol.

In some embodiments, the second molecule is selected from a terpene, terpene alcohol, terpenoid, or terpene oxidation product. In some specific embodiments, the second molecule is selected from the terpenes beta-caryophyllene, humulene, myrcene, limonene, alpha-terpinene, delta-3-carene, and terpinolene; the terpene alcohols guaiol, alpha-bisabolol, linalool, alpha-terpineol, nerolidol, borneol, and isopulegol; the terpenoids beta-caryophyllene oxide and eucalyptol; and the terpene oxidation product para-cymene. In some very specific embodiments, the second molecule is beta-caryophyllene.

In some preferred embodiments, the cannabinoid molecule is cannabidiol, and the second molecule is tetrahydrocannabinol.

In some embodiments, the cannabinoid molecule is cannabidiol, and the second molecule is cannabichromene.

In some embodiments, the cannabinoid molecule is cannabidivarin, and the second molecule is tetrahydrocannabivarin.

In some embodiments, the cannabinoid molecule is cannabigerol, and the second molecule is beta-caryophyllene.

In some embodiments, the cannabinoid molecule is cannabigerovarin, and the second molecule is beta-caryophyllene.

In general, a starting composition comprises a decarboxylated cannabinoid extract that is wholly or partially dissolved in an alcohol. The starting composition can optionally comprise other molecules (such as water), which may be present either in a decarboxylated cannabinoid extract or in an alcohol, or which may be otherwise added for any reason. The ranges set forth in this patent document are intended to cover both embodiments that might inevitably occur when practicing the full scope of the methods disclosed in this patent document as well embodiments that are viable workarounds to the straightforward practice of the disclosed methods.

In some embodiments, the method comprises dissolving a composition comprising the cannabinoid molecule and the second molecule in a liquid comprising an alcohol to produce a starting composition, in which the liquid comprises the alcohol at a concentration of at least 50 percent by mass. In some very specific embodiments, the method comprises dissolving a composition comprising the cannabinoid molecule and the second molecule in a liquid comprising an alcohol to produce a starting composition, in which the liquid comprises the alcohol at a concentration of at least 90 percent by mass.

In some embodiments, the method comprises dissolving a composition comprising the cannabinoid molecule and the second molecule in a liquid comprising an alcohol to produce a starting composition, in which: the composition is a decarboxylated cannabinoid extract; and the liquid comprises the alcohol at a concentration of at least 50 percent by mass. In some very specific embodiments, the method comprises dissolving a composition comprising the cannabinoid molecule and the second molecule in a liquid comprising an alcohol to produce a starting composition, in which: the composition is a decarboxylated cannabinoid extract; and the liquid comprises the alcohol at a concentration of at least 90 percent by mass.

In some embodiments, the decarboxylated cannabinoid extract is a decarboxylated crude *cannabis* extract, decarboxylated full-spectrum *cannabis* extract, decarboxylated broad-spectrum *cannabis* extract, or decarboxylated *cannabis* extract distillate. In some specific embodiments, the decarboxylated cannabinoid extract is a decarboxylated crude industrial hemp extract, decarboxylated full-spectrum industrial hemp extract, decarboxylated broad-spectrum industrial hemp extract, or decarboxylated industrial hemp extract distillate.

In some embodiments, the method comprises decarboxylating a cannabinoid extract to produce the decarboxylated cannabinoid extract. In some specific embodiments, the method comprises decarboxylating a cannabinoid extract to produce the decarboxylated cannabinoid extract, in which decarboxylating the cannabinoid extract comprises heating the cannabinoid extract.

In some embodiments, the liquid comprises the alcohol at a concentration of 55 percent to 100 percent by mass. In some specific embodiments, the liquid comprises the alcohol at a concentration of 75 percent to 100 percent by mass. In very specific embodiments, the liquid comprises the alcohol at a concentration of 90 percent to 100 percent by mass.

In some embodiments, the method comprises providing a starting composition comprising an alcohol, the cannabinoid molecule, and the second molecule. In some specific embodiments, the method comprises providing a starting composition comprising a decarboxylated cannabinoid extract and an alcohol, in which: the starting composition comprises the cannabinoid molecule and the second molecule; and both the cannabinoid molecule and the second molecule originate from the decarboxylated cannabinoid extract. In some very specific embodiments, the method comprises providing a starting composition comprising a decarboxylated hemp extract and an alcohol, in which: the starting composition comprises the cannabinoid molecule and the second molecule; and both the cannabinoid molecule and the second molecule originate from the decarboxylated hemp extract.

In some embodiments, the alcohol is selected from methanol, ethanol, isopropanol, propylene glycol, and propane-1, 3-diol. In some specific embodiments, the alcohol is certified USDA organic ethanol. "USDA" is an acronym for "United States Department of Agriculture," which provides rules and regulations to certify products as organic under United States law.

In preferred embodiments, the alcohol is ethanol.

In some embodiments, the starting composition is a liquid, and the liquid is an alcohol phase.

In some embodiments, the starting composition comprises a liquid phase, and the liquid phase is an alcohol phase. In some specific embodiments, the starting composition comprises a liquid phase and a solid phase; the liquid phase and the solid phase are in physical communication; the solid phase is suspended in the liquid phase; and the liquid phase is an alcohol phase. In some very specific embodiments, the starting composition comprises a liquid phase and a solid phase; the liquid phase and the solid phase are in physical communication; the solid phase is partially suspended in the liquid phase; and the liquid phase is an alcohol phase.

In some embodiments, the starting composition comprises a liquid phase; the liquid phase is an alcohol phase; and the alcohol phase comprises the alcohol, the cannabinoid molecule, and the second molecule of the starting composition.

In some embodiments, the starting composition comprises a liquid phase; the liquid phase is an alcohol phase; and the alcohol phase comprises the alcohol, the plurality of cannabinoid molecules, and the plurality of second molecules of the starting composition.

In some embodiments, the starting composition comprises a liquid phase; the liquid phase is an alcohol phase; and the alcohol phase comprises (i) at least some of the alcohol of the starting composition; (ii) at least some of the cannabinoid molecule of the starting composition; and (iii) at least some of the second molecule of the starting composition. In some specific embodiments, the starting composition comprises a liquid phase; the liquid phase is an alcohol phase; and the alcohol phase comprises (i) at least 90 percent of the alcohol of the starting composition; (ii) at least 50 percent of the cannabinoid molecule of the starting composition; and (iii) at least some of the second molecule of the starting composition. In some very specific embodiments, the starting composition comprises a liquid phase; the liquid phase is an alcohol phase; and the alcohol phase comprises (i) 90 percent to 100 percent of the alcohol of the starting composition; (ii) 50 percent to 100 percent of the cannabinoid molecule of the starting composition; and (iii) 50 percent to 100 percent of the second molecule of the starting composition. In some very specific embodiments, the starting composition comprises a liquid phase; the liquid phase is an alcohol phase; and the alcohol phase comprises (i) at least 90 percent of the alcohol of the starting composition; (ii) at least 90 percent of the cannabinoid molecule of the starting composition; and (iii) at least 50 percent of the second molecule of the starting composition.

In some preferred embodiments, the alcohol is ethanol; the starting composition comprises the ethanol at a concentration of 35 percent to 90 percent by mass; the cannabinoid molecule is cannabidiol; the starting composition comprises the cannabidiol at a concentration of 5 percent to 60 percent by mass; the second molecule is tetrahydrocannabinol; and the starting composition comprises the tetrahydrocannabinol at a concentration of to 0.1 percent to 5 percent by mass.

In some embodiments, the alcohol of the alcohol phase is a solvent, and the cannabinoid molecule of the alcohol phase is a solute that is dissolved in the alcohol of the alcohol phase.

In some embodiments, the alcohol of the alcohol phase is a solvent, and the second molecule of the alcohol phase is a solute that is dissolved in the alcohol of the alcohol phase.

In some preferred embodiments, the alcohol is ethanol; the starting composition comprises the ethanol at a concentration of 35 percent to 90 percent by mass; the starting composition comprises a plurality of cannabinoid molecules that comprises cannabidiol and cannabigerol; the starting composition comprises the cannabidiol at a concentration of 5 percent to 60 percent by mass; the starting composition comprises the cannabigerol at a concentration of 0.05 percent to 3 percent by mass; the starting composition comprises a plurality of second molecules that comprises tetrahydrocannabinol, cannabichromene, and beta-caryophyllene; the starting composition comprises the tetrahydrocannabinol at a concentration of to 0.1 percent to 5 percent by mass; the starting composition comprises the cannabichromene at a concentration of 0.1 percent to 5 percent by mass; and the starting composition comprises the beta-caryophyllene at a concentration of 0.1 percent to 5 percent by mass.

In some embodiments, the alcohol phase comprises (a) at least some of the cannabichromene of the plurality of second molecules of the starting composition, (b) at least some of the cannabigerol of the plurality of cannabinoid molecules of the starting composition, and (c) at least some of the beta-caryophyllene of the plurality of the second molecules of the starting composition; the alcohol is ethanol; the cannabichromene of the alcohol phase is a solute that is dissolved in the ethanol of the alcohol phase; the cannabigerol of the alcohol phase is a solute that is dissolved in the ethanol of the alcohol phase; and the beta-caryophyllene of the alcohol phase is a solute that is dissolved in the ethanol of the alcohol phase.

In some embodiments, the alcohol of the alcohol phase is present in the alcohol phase at a concentration of at least 20 percent and no greater than 99 percent by mass. In some specific embodiments, the alcohol of the alcohol phase is present in the alcohol phase at a concentration of at least 35 percent and no greater than 99 percent by mass. In some very specific embodiments, the alcohol of the alcohol phase is present in the alcohol phase at a concentration of at least 35 percent and no greater than 80 percent by mass.

In some embodiments, the starting composition comprises the cannabinoid molecule at a concentration of at least 0.65 percent and no greater than 65 percent by mass. In some specific embodiments, the starting composition comprises the cannabinoid molecule at a concentration of at least 5 percent and no greater than 60 percent by mass. In some very specific embodiments, the starting composition comprises the cannabinoid molecule at a concentration of at least 10 percent and no greater than 55 percent by mass.

In some embodiments, the starting composition comprises the second molecule at a concentration of at least 0.065 percent and no greater than 6.5 percent by mass. In some specific embodiments, the starting composition comprises the second molecule at a concentration of at least 0.1 percent and no greater than 6 percent by mass. In some very specific embodiments, the starting composition comprises the second molecule at a concentration of at least 0.1 percent and no greater than 5 percent by mass.

In some embodiments, the starting composition comprises cannabidiol and tetrahydrocannabinol at a cannabidiol-to-tetrahydrocannabinol ratio of at least 10:1 and less than 350:1 by mass.

In some embodiments, the starting composition has a temperature of at least −79 degrees Celsius and no greater than 79 degrees Celsius. In some specific embodiments, the starting composition has a temperature of at least 19 degrees Celsius and no greater than 25 degrees Celsius.

In some embodiments, the cannabinoid molecule has a solubility in the alcohol phase of the starting composition that is greater than 2 grams per liter. In some specific embodiments, the cannabinoid molecule has a solubility in the alcohol phase of the starting composition that is greater than 10 grams per liter. In some specific embodiments, the cannabinoid molecule has a solubility in the alcohol phase of the starting composition that is greater than 50 grams per liter.

In some embodiments, the second molecule has a solubility in the alcohol phase of the starting composition that is greater than 2 grams per liter. In some specific embodiments, the second molecule has a solubility in the alcohol phase of the starting composition that is greater than 10 grams per liter. In some very specific embodiments, the second molecule has a solubility in the alcohol phase of the starting composition that is greater than 50 grams per liter.

In some embodiments, the method comprises decreasing the solubility of the second molecule in the alcohol phase of the starting composition by combining the alcohol phase and a solubility-regulating composition to (a) drive a portion of the second molecule of the alcohol phase out of the alcohol phase and (b) produce a heterogeneous composition.

In some embodiments, the solubility-regulating composition comprises water. In some specific embodiments, the solubility-regulating composition comprises water at a concentration of at least 50 percent by mass. In some very specific embodiments, the solubility-regulating composition consists essentially of water.

In general, the solubility-regulating composition allows the adjustment of the hydrophilicity, hydrogen cation concentration, and ionic strength of a liquid phase, which allows the precise control of the solubility of various molecules (and ions) in the liquid phase.

In some embodiments, the solubility-regulating composition comprises the water at a concentration by mass that is greater than the concentration by mass of any water that is present in the alcohol phase of the starting composition such that the combination of the alcohol phase and the solubility-regulating composition has a greater concentration of water than the alcohol phase of the starting composition.

In some specific embodiments, the starting composition comprises water at a concentration of less than 25 percent by mass; and the solubility-regulating composition comprises water at a concentration of at least 50 percent by mass. In some very specific embodiments, the starting composition comprises water at a concentration of less than 10 percent by mass; and the solubility-regulating composition comprises water at a concentration of at least 95 percent by mass.

In some embodiments, the heterogeneous composition comprises each of (a) the alcohol of the starting composition, (b) the cannabinoid molecule of the starting composition, (c) the second molecule of the starting composition, and (d) the water of the solubility-regulating composition.

In some specific embodiments, the alcohol is ethanol; the aqueous phase of the heterogeneous composition has a hydrogen cation concentration of at least 10 picomolar and no greater than 1 micromolar; the aqueous phase of the heterogeneous composition comprises ethoxide anion and hydroxide anion at a combined concentration of at least 2 nanomolar and no greater than 10 millimolar; and combining the alcohol phase and the solubility-regulating composition results in an ethoxide anion concentration of the aqueous phase of the heterogeneous composition that is no greater than half the ethoxide anion concentration of the alcohol phase of the starting composition.

In some specific embodiments, the alcohol phase of the starting composition has an ionic strength that is less than 100 millimolar; the aqueous phase of the heterogeneous composition has an ionic strength that is greater than 100 millimolar; the ionic strength of the aqueous phase of the heterogeneous composition is at least 10 times greater than the ionic strength of the alcohol phase of the starting composition; and decreasing the solubility of the second molecule in the alcohol phase comprises increasing the ionic strength of the alcohol phase by combining the alcohol phase with the solubility-regulating composition.

In some preferred embodiments, the heterogeneous composition comprises an aqueous phase and a lipid phase. In some specific embodiments, the heterogeneous composition comprises an aqueous phase and a lipid phase, in which the lipid phase is enriched in the second molecule. In some very specific embodiments, the heterogeneous composition comprises an aqueous phase and a lipid phase, in which the lipid phase is a tetrahydrocannabinol-enriched lipid phase.

In some embodiments, the aqueous phase is a liquid.

In some embodiments, the aqueous phase comprises greater than 50 percent of the cannabinoid molecule of the heterogeneous composition. In some specific embodiments, the aqueous phase comprises greater than 75 percent of the cannabinoid molecule of the heterogeneous composition. In some very specific embodiments, the aqueous phase comprises greater than 90 percent of the cannabinoid molecule of the heterogeneous composition.

In some embodiments, the aqueous phase comprises greater than 50 percent of the alcohol of the heterogeneous composition. In some specific embodiments, the aqueous phase comprises greater than 75 percent of the alcohol of the heterogeneous composition. In some very specific embodiments, the aqueous phase comprises greater than 90 percent of the alcohol of the heterogeneous composition.

In some embodiments, the aqueous phase comprises at least 95 percent of the water of the heterogeneous composition.

In some embodiments, either (a) the alcohol of the aqueous phase is a solvent, and the water of the aqueous phase is a solute that is dissolved in the ethanol of the aqueous phase, or (b) the water of the aqueous phase is a solvent, and the alcohol of the aqueous phase is a cosolvent.

The term "solvent" refers to the most abundant molecule in a composition, by mass, that is a liquid at the temperature of the composition. The solvent of a heterogeneous composition is typically the alcohol of the heterogeneous composition; however, in some embodiments, the water of a heterogeneous composition is present at a greater concentration by mass than the alcohol of the heterogeneous composition such that the water is a solvent and the alcohol is a cosolvent. The terms "alcohol phase" and "aqueous phase" distinguish the liquid phase of the starting composition from the liquid phase of the heterogeneous composition, and neither term requires a specific type of solvent; the solvent of the "alcohol phase" is nevertheless generally an alcohol, and the solvent of the "aqueous phase" is either an alcohol or water as set forth above. The term "cosolvent" refers to the second most abundant molecule is a composition, by mass, that both (a) is a liquid at the temperature of the composition and (b) is capable of dissolving a solute of the composition in the absence of the solvent. A cosolvent of this patent document is typically an alcohol.

In some embodiments, the cannabinoid molecule of the heterogeneous composition has a solubility in the aqueous phase that is greater than 2 grams per liter. In some specific embodiments, the cannabinoid molecule of the heterogeneous composition has a solubility in the aqueous phase that is greater than 10 grams per liter. In some very specific embodiments, the cannabinoid molecule of the heterogeneous composition has a solubility in the aqueous phase that is greater than 50 grams per liter.

In some embodiments, the cannabinoid molecule is a solute that is dissolved in the solvent of the aqueous phase.

In some embodiments, the second molecule of the heterogeneous composition has a solubility in the aqueous phase that is less than 50 grams per liter. In some specific embodiments, the second molecule of the heterogeneous composition has a solubility in the aqueous phase that is less than 10 grams per liter. In some very specific embodiments, the second molecule of the heterogeneous composition has a solubility in the aqueous phase that is less than 2 grams per liter.

In some embodiments, the aqueous phase comprises any cannabidiol of the aqueous phase and any tetrahydrocannabinol that is dissolved in the solvent of the aqueous phase at a cannabidiol-to-tetrahydrocannabinol ratio that is greater than 350:1 by mass.

In some embodiments, the lipid phase comprises greater than 50 percent of the second molecule of the heterogeneous composition. In some specific embodiments, the lipid phase comprises greater than 65 percent of the second molecule of the heterogeneous composition. In some very specific embodiments, the lipid phase comprises greater than 80 percent of the second molecule of the heterogeneous composition.

The methods of this patent document would ideally result in a cannabinoid molecule is freely soluble in the aqueous phase of the heterogeneous composition and a second molecule that is insoluble in the aqueous phase such that 100 percent of the cannabinoid molecule partitions into the aqueous phase and 100 percent of the second molecule partitions into the lipid phase; however, less than ideal results are obtained during real-world implementation. Methods in which greater than 50 percent of the cannabinoid molecule partitions into the aqueous phase and greater than 50 percent of the second molecule partitions into the lipid phase are featured in this patent document because these methods display utility. The gram-per-liter solubilities set forth in this patent document help delineate commercial utility from theoretical utility.

In some embodiments, the starting composition comprises a plurality of cannabinoid molecules; the plurality of cannabinoid molecules comprises cannabidiol and cannabigerol; the starting composition comprises a plurality of second molecules; the plurality of second molecules comprises tetrahydrocannabinol, cannabichromene, and beta-caryophyllene; the heterogeneous composition comprises each of (a) the cannabidiol of the plurality of cannabinoid molecules of the starting composition, (b) the cannabigerol of the plurality of cannabinoid molecules of the starting composition, (c) the tetrahydrocannabinol of the plurality of second molecules of the starting composition, (d) the cannabichromene of the plurality of second molecules of the starting composition, and (e) the beta-caryophyllene of the plurality of second molecules of the starting composition; the combining of the alcohol phase and the solubility-regulating composition drives a portion of the tetrahydrocannabinol of the alcohol phase out of the alcohol phase; the combining of the alcohol phase and the solubility-regulating composition drives a portion of the cannabichromene of the alcohol phase out of the alcohol phase; the combining of the alcohol phase and the solubility-regulating composition drives a portion of the beta-caryophyllene of the alcohol phase out of the alcohol phase; the aqueous phase comprises greater than 65 percent of the cannabidiol of the heterogeneous composition; the cannabidiol of the aqueous phase is a solute that is dissolved in the solvent of the aqueous phase; the aqueous phase comprises greater than 65 percent of the cannabigerol of the heterogeneous composition; the cannabigerol of the aqueous phase is a solute that is dissolved in the solvent of the aqueous phase; the lipid phase comprises greater than 65 percent of the tetrahydrocannabinol of the heterogeneous composition; the lipid phase comprises greater than 65 percent of the cannabichromene of the heterogeneous composition; and the lipid phase comprises greater than 65 percent of the beta-caryophyllene of the heterogeneous composition. In some specific embodiments, the starting composition comprises a plurality of cannabinoid molecules; the plurality of cannabinoid molecules comprises cannabidiol and cannabigerol; the starting composition comprises a plurality of second molecules; the plurality of second molecules comprises tetrahydrocannabinol, cannabichromene, and beta-caryophyllene; the heterogeneous composition comprises each of (a) the cannabidiol of the plurality of cannabinoid molecules of the starting composition, (b) the cannabigerol of the plurality of cannabinoid molecules of the starting composition, (c) the tetrahydrocannabinol of the plurality of second molecules of the starting composition, (d) the cannabichromene of the plurality of second molecules of the starting composition, and (e) the beta-caryophyllene of the plurality of second molecules of the starting composition; the tetrahydrocannabinol of the starting composition has a solubility in the alcohol phase that is greater than 10 grams per liter; the tetrahydrocannabinol of the heterogeneous composition has a solubility in the aqueous phase that is less than 10 grams per liter; the combining of the alcohol phase and the solubility-regulating composition drives a portion of the tetrahydrocannabinol of the alcohol phase out of the alcohol phase; the cannabichromene of the starting composition has a solubility in the alcohol phase that is greater than 10 grams per liter; the cannabichromene of the heterogeneous composition has a solubility in the aqueous phase that is less than 10 grams per liter; the combining of the alcohol phase and the solubility-regulating composition drives a portion of the cannabichromene of the alcohol phase out of the alcohol phase; the beta-caryophyllene of the starting composition has a solubility in the alcohol phase that is greater than 5 grams per liter; the beta-caryophyllene of the heterogeneous composition has a solubility in the aqueous phase that is less than 5 grams per liter; the combining of the alcohol phase and the solubility-regulating composition drives a portion of the beta-caryophyllene of the alcohol phase out of the alcohol phase; the cannabidiol of the starting composition has a solubility in the alcohol phase that is greater than 10 grams per liter; the cannabidiol of the heterogeneous composition has a solubility in the aqueous phase that is greater than 10 grams per liter; the aqueous phase comprises greater than 65 percent of the cannabidiol of the heterogeneous composition; the cannabidiol of the aqueous phase is a solute that is dissolved in the solvent of the aqueous phase; the cannabigerol of the starting composition has a solubility in the alcohol phase that is greater than 10 grams per liter; the cannabigerol of the heterogeneous composition has a solubility in the aqueous phase that is greater than 10 grams per liter; the aqueous phase comprises greater than 65 percent of the cannabigerol of the heterogeneous composition; the cannabigerol of the aqueous phase is a solute that is dissolved in the solvent of the aqueous phase; the lipid phase comprises greater than 65 percent of the tetrahydrocannabinol of the heterogeneous composition; the lipid phase comprises greater than 65 percent of the cannabichromene of the heterogeneous composition; and the lipid phase comprises greater than 65 percent of the beta-caryophyllene of the heterogeneous composition.

In some embodiments, the method comprises selecting either a fraction or all of the heterogeneous composition for further processing to produce a fractionated heterogeneous composition. The heterogeneous composition is optionally fractionated to process different portions of the heterogeneous composition in series (such as when the capacity of downstream steps is limited relative to capacity of upstream steps) or in parallel (such as in different centrifuge tubes). The fractionation steps are disclosed in part to claim workarounds; if a fractionation step were not included in the claims, then an unscrupulous individual might avoid literally infringing a claimed method by merely discard a portion of a composition while otherwise performing the claimed method. A fractionated heterogeneous composition is therefore either (i) exactly the same as the heterogeneous composition or (ii) a portion of the heterogeneous composition, in which the portion is either (a) a portion that is processed in series or parallel with other portions or (b) simply the portion that is further-processed according to a claimed method.

In some embodiments, the fractionated heterogeneous composition comprises a fractionated aqueous phase and a fractionated lipid phase. In some specific embodiments, the fractionated heterogeneous composition comprises a fractionated aqueous phase and a fractionated lipid phase, in which the fractionated lipid phase is enriched in the second molecule. In some very specific embodiments, the fractionated heterogeneous composition comprises a fractionated aqueous phase and a fractionated lipid phase, and the fractionated lipid phase is a fractionated tetrahydrocannabinol-enriched lipid phase.

In some embodiments, the fractionated aqueous phase consists of either a fraction or all of the aqueous phase of the heterogeneous composition; the fractionated aqueous phase comprises either a fraction or all of the cannabinoid molecule of the aqueous phase; the fractionated aqueous phase comprises either a fraction or all of the alcohol of the aqueous phase; the fractionated aqueous phase comprises either a fraction or all of the water of the aqueous phase; the fractionated lipid phase consists of either a fraction or all of the lipid phase of the heterogeneous composition; and the fractionated lipid phase comprises either a fraction or all of the second molecule of the lipid phase of the heterogeneous composition. In some specific embodiments, the fractionated aqueous phase consists of the aqueous phase of the heterogeneous composition; the fractionated aqueous phase comprises all of the cannabinoid molecule of the aqueous phase; the fractionated aqueous phase comprises all of the alcohol of the aqueous phase; the fractionated aqueous phase comprises all of the water of the aqueous phase; the fractionated lipid phase consists of all of the lipid phase of the heterogeneous composition; and the fractionated lipid phase comprises all of the second molecule of the lipid phase of the heterogeneous composition. In some specific embodiments, the fractionated aqueous phase consists of a fraction of the aqueous phase of the heterogeneous composition; the fractionated aqueous phase comprises a fraction of the cannabinoid molecule of the aqueous phase; the fractionated aqueous phase comprises a fraction of the alcohol of the aqueous phase; the fractionated aqueous phase comprises a fraction of the water of the aqueous phase; the fractionated lipid phase consists of a fraction of the lipid phase of the heterogeneous composition; and the fractionated lipid phase comprises a fraction of the second molecule of the lipid phase of the heterogeneous composition.

In some embodiments, the method comprises mechanically separating the fractionated aqueous phase of the fractionated heterogeneous composition from the fractionated lipid phase of the fractionated heterogeneous composition to mechanically separate the cannabinoid molecule of the fractionated aqueous phase from the second molecule of the fractionated lipid phase.

The verb "separate" and its derivatives do not require complete separation, for example, because perfect separation lacks real-world feasibility, and thus, the verb "separate" and its derivatives refer to partial separation as allowed by the specific context of each occurrence of the word "separate" or its derivative in this patent document.

In some embodiments, the mechanical separation of the fractionated aqueous phase of the fractionated heterogeneous composition from the fractionated tetrahydrocannabinol-enriched lipid phase of the fractionated heterogeneous composition comprises centrifuging the fractionated heterogeneous composition.

In some embodiments, the method comprises selecting either a fraction or all of the fractionated aqueous phase for further processing to produce a second fractionated aqueous phase. The fractionated aqueous phase is optionally fractionated to process different portions of the fractionated aqueous phase in series (such as when the capacity of downstream steps is limited relative to capacity of upstream steps) or in parallel (such as in different centrifuge tubes). A second fractionated aqueous phase is either (i) exactly the same as the fractionated aqueous phase or (ii) a portion of the fractionated aqueous phase, in which the portion is either (a) a portion that is processed in series or parallel with other portions or (b) simply the portion that is further-processed according to a claimed method.

In some embodiments, the second fractionated aqueous phase comprises either a fraction or all of the cannabinoid molecule of the fractionated aqueous phase; the second fractionated aqueous phase comprises either a fraction or all of the alcohol of the fractionated aqueous phase; and the second fractionated aqueous phase comprises either a fraction or all of the water of the fractionated aqueous phase. In some specific embodiments, the second fractionated aqueous phase comprises all of the cannabinoid molecule of the fractionated aqueous phase; the second fractionated aqueous phase comprises all of the alcohol of the fractionated aqueous phase; and the second fractionated aqueous phase comprises all of the water of the fractionated aqueous phase. In some specific embodiments, the second fractionated aqueous phase comprises a fraction of the cannabinoid molecule of the fractionated aqueous phase; the second fractionated aqueous phase comprises a fraction of the alcohol of the fractionated aqueous phase; and the second fractionated aqueous phase comprises a fraction of the water of the fractionated aqueous phase.

In some embodiments, the method comprises separating (a) a majority of the alcohol of the second fractionated aqueous phase and a majority of the water of the second fractionated aqueous phase from (b) a majority of the cannabinoid molecule of the second fractionated aqueous phase to produce a product.

In some embodiments, the separation of (a) the majority of the alcohol of the second fractionated aqueous phase and the majority of the water of the second fractionated aqueous phase from (b) the majority of the cannabinoid molecule of the second fractionated aqueous phase comprises (i) vaporizing the majority of the alcohol of the second fractionated aqueous phase to produce alcohol vapor, (ii) vaporizing the majority of the water of the second fractionated aqueous phase to produce water vapor, and (iii) removing both the alcohol vapor and the water vapor from the second fractionated aqueous phase using a vacuum; the vaporizing and removing are performed under conditions that do not vaporize and remove the majority of the cannabinoid molecule of the second fractionated aqueous phase from the second fractionated aqueous phase; and the product consists of the portion of the second fractionated aqueous phase that is not both vaporized and removed from the second fractionated aqueous phase.

In some embodiments, the separation of (a) the majority of the alcohol of the second fractionated aqueous phase and the majority of the water of the second fractionated aqueous phase from (b) the majority of the cannabinoid molecule of the second fractionated aqueous phase comprises combining the second fractionated aqueous phase and a second solubility-regulating composition to (i) drive a portion of the cannabinoid molecule of the second fractionated aqueous phase out of the second fractionated aqueous phase, and (ii) produce a second heterogeneous composition.

In some embodiments, the second solubility-regulating composition comprises water at a concentration by mass that is greater than the concentration by mass of the water that is present in the second fractionated aqueous phase such that the combination of the second fractionated aqueous phase and the second solubility-regulating composition has a greater concentration of water than the second fractionated aqueous phase.

In some embodiments, the second heterogeneous composition comprises (a) substantially all of the alcohol of the second fractionated aqueous phase, (b) substantially all of the cannabinoid molecule of the second fractionated aqueous phase, (c) substantially all of the water of the second fractionated aqueous phase, and (e) the water of the second solubility-regulating composition.

In some embodiments, the second heterogeneous composition comprises a residual aqueous phase and a second lipid phase. In some specific embodiments, the second heterogeneous composition comprises a residual aqueous phase and a second lipid phase, in which the second lipid phase is enriched in the cannabinoid molecule. In some very specific embodiments, the second heterogeneous composition comprises a residual aqueous phase and a second lipid phase, in which the second lipid phase is a cannabidiol-enriched lipid phase.

In some embodiments, the residual aqueous phase is a liquid.

In some embodiments, the residual aqueous phase comprises greater than 50 percent of the alcohol of the second heterogeneous composition. In some embodiments, the residual aqueous phase comprises greater than 75 percent of the alcohol of the second heterogeneous composition. In some embodiments, the residual aqueous phase comprises greater than 90 percent of the alcohol of the second heterogeneous composition.

In some embodiments, the residual aqueous phase comprises greater than 95 percent of the water of the second heterogeneous composition.

In some embodiments, the cannabinoid molecule is cannabidiol; the cannabidiol of the second heterogeneous composition has a solubility in the residual aqueous phase that is less than 10 grams per liter; and the second lipid phase comprises greater than 80 percent of the cannabidiol of the second heterogeneous composition.

In some embodiments, the second lipid phase comprises any cannabidiol of the second lipid phase and any tetrahydrocannabinol that is present in the second lipid phase at a cannabidiol-to-tetrahydrocannabinol ratio that is greater than 350:1 by mass.

In some embodiments, the separation of (a) the majority of the alcohol of the second fractionated aqueous phase and the majority of the water of the second fractionated aqueous phase from (b) the majority of the cannabinoid molecule of the second fractionated aqueous phase further comprises mechanically separating the residual aqueous phase of the second heterogeneous composition from the second lipid phase of the second heterogeneous composition.

In some embodiments, the mechanical separation of the residual aqueous phase of the second heterogeneous composition from the second lipid phase of the second heterogeneous composition comprises centrifuging the second heterogeneous composition to produce (a) an aqueous liquid, which comprises the majority of the alcohol of the second fractionated aqueous phase and the majority of the water of the second fractionated aqueous phase, and (b) an oil and any precipitate, which comprises the majority of the cannabinoid molecule of the second fractionated aqueous phase.

In some embodiments, the separation of (a) the majority of the alcohol of the second fractionated aqueous phase and the majority of the water of the second fractionated aqueous phase from (b) the majority of the cannabinoid molecule of the second fractionated aqueous phase comprises combining the second fractionated aqueous phase and a second solubility-regulating composition to (i) drive a portion of the cannabinoid molecule of the second fractionated aqueous phase out of the second fractionated aqueous phase and (ii) produce a second heterogeneous composition; the second heterogeneous composition comprises (a) substantially all of the alcohol of the second fractionated aqueous phase, (b) substantially all of the cannabinoid molecule of the second fractionated aqueous phase, and (c) substantially all of the water of the second fractionated aqueous phase; the aqueous phase of the heterogeneous composition has an ionic strength that is no greater than 100 millimolar; the second fractionated aqueous phase has an ionic strength that is no greater than 100 millimolar; the second heterogeneous composition comprises a residual aqueous phase and a second lipid phase; the residual aqueous phase of the second heterogeneous composition has an ionic strength of at least 100 millimolar; the ionic strength of the residual aqueous phase of the second heterogeneous composition is at least 10 times greater than the ionic strength of the aqueous phase of the heterogeneous composition; the residual aqueous phase is a liquid; the residual aqueous phase comprises greater than 50 percent of the alcohol of the second heterogeneous composition; the residual aqueous phase comprises greater than 95 percent of the water of the second heterogeneous composition; the cannabinoid molecule of the second heterogeneous composition has a solubility in the residual aqueous phase that is less than 10 grams per liter; the second lipid phase comprises greater than 80 percent of the cannabinoid molecule of the second heterogeneous composition; the second lipid phase comprises the cannabinoid molecule of the second lipid phase and any tetrahydrocannabinol that is present in the second lipid phase at a cannabinoid-molecule-to-tetrahydrocannabinol ratio that is greater than 350:1 by mass; the separation of (a) the majority of the alcohol of the second fractionated aqueous phase and the majority of the water of the second fractionated aqueous phase from (b) the majority of the cannabinoid molecule of the second fractionated aqueous phase further comprises mechanically separating the residual aqueous phase of the second heterogeneous composition from the second lipid phase of the second heterogeneous composition; and the product consists essentially of the portion of the second lipid phase that is mechanically separated from the residual aqueous phase.

In some embodiments, the product comprises the cannabinoid molecule of the second fractionated aqueous phase.

In some embodiments, the product comprises the cannabinoid molecule at a concentration of at least 50 percent by mass. In some specific embodiments, the product comprises the cannabinoid molecule at a concentration of at least 75 percent by mass. In some very specific embodiments, the product comprises the cannabinoid molecule at a concentration of at least 90 percent by mass.

In some embodiments, the product comprises cannabidiol. In some specific embodiments, the product comprises cannabidiol and cannabigerol. In some embodiments, the product comprises cannabidivarin and cannabigerovarin. In some very specific embodiments, the product comprises cannabidiol at a concentration of at least 75 percent by mass and cannabigerol at a concentration of at least 0.05 percent and no greater than 5 percent by mass.

In some embodiments, the product lacks the second molecule at a concentration greater than 0.3 percent by mass.

In some embodiments, the product lacks tetrahydrocannabinol at a concentration greater than 0.3 percent by mass.

In some embodiments, the product comprises cannabidiol and any tetrahydrocannabinol at a cannabidiol-to-tetrahydrocannabinol ratio that is greater that 350:1 by mass.

In some embodiments, the product lacks the alcohol at a concentration greater than 5 percent by mass. In some specific embodiments, the product lacks the alcohol at a concentration greater than 1 percent by mass. In some very specific embodiments, the product lacks the alcohol at a concentration greater than 0.2 percent by mass.

In some embodiments, the product lacks water at a concentration greater than 5 percent by mass. In some specific embodiments, the product lacks water at a concentration greater than 1 percent by mass. In some very specific embodiments, the product lacks water at a concentration greater than 0.2 percent by mass.

In some embodiments, the product consists essentially of the portion of the second lipid phase that is mechanically separated from the residual aqueous phase.

In some embodiments, the product consists essentially of the oil and any precipitate that is produced, for example, by separating the both the water and alcohol of the residual aqueous phase of the second heterogeneous composition from the second lipid phase of the second heterogeneous composition.

In some embodiments, the product lacks cannabichromene at a concentration greater than 5 percent by mass.

In some embodiments, the product lacks beta-caryophyllene at a concentration greater than 5 percent by mass.

In some embodiments, the product is obtained at a temperature of at least 20 degrees Celsius and no greater than 65 degrees Celsius. In some embodiments, the starting composition has a temperature of at least 20 degrees Celsius and no greater than 65 degrees Celsius; and the product is produced at a temperature of at least 20 degrees Celsius and no greater than 65 degrees Celsius.

In some embodiments, the product comprises an oil, and the oil is a supercooled liquid. In some specific embodiments, the product comprises an oil; the oil is a supercooled liquid; and the temperature of the product is below the freezing point of the oil.

In some embodiments, the product is produced at a temperature that is less than the freezing point of the cannabinoid molecule; the product comprises a glass; the glass comprises greater than 50 percent of the cannabinoid molecule of the product; the glass comprises the cannabinoid molecule at a concentration of at least 50 percent by mass; the glass has a glass-transition temperature that is less than the freezing point of cannabinoid molecule; the glass lacks a freezing point; and the glass lacks a melting point. In some specific embodiments, the cannabinoid molecule is cannabidiol; the product is produced at a temperature that is less than the freezing point of the cannabidiol; the product comprises a glass; the glass comprises greater than 50 percent of the cannabidiol of the product; the glass comprises the cannabidiol at a concentration of at least 50 percent by mass; the glass has a glass-transition temperature that is less than the freezing point of cannabidiol; the glass lacks a freezing point; and the glass lacks a melting point.

In some embodiments, the product is produced at a temperature that is less than the freezing point of the cannabinoid molecule; the product comprises crystals; the crystals comprise greater than 50 percent of the cannabinoid molecule of the product; the crystals comprise the cannabinoid molecule at a concentration of at least 50 percent by mass; the crystals have a melting point; and the crystals lack a glass-transition temperature. In some specific embodiments, the cannabinoid molecule is cannabidiol; the product is produced at a temperature that is less than the freezing point of the cannabidiol; the product comprises crystals; the crystals comprise greater than 50 percent of the cannabidiol of the product; the crystals comprise the cannabidiol at a concentration of at least 50 percent by mass; the crystals have a melting point; and the crystals lack a glass-transition temperature.

In some embodiments, the product is produced at a temperature that is less than the freezing point of the cannabinoid molecule; the product comprises an oil; the oil comprises greater than 50 percent of the cannabinoid molecule of the product; the oil comprises the cannabinoid molecule at a concentration of at least 50 percent by mass; the oil is a supercooled liquid; the oil has a freezing point; and the oil lacks a glass-transition temperature. In some specific embodiments, the cannabinoid molecule is cannabidiol; the product is produced at a temperature that is less than the freezing point of cannabidiol; the product comprises an oil; the oil comprises greater than 50 percent of the cannabidiol of the product; the oil comprises the cannabidiol at a concentration of at least 50 percent by mass; the oil is a supercooled liquid; the oil has a freezing point; and the oil lacks a glass-transition temperature.

In some embodiments, the starting composition comprises a plurality of second molecules; the plurality of second molecules comprises tetrahydrocannabinol and (6aS,10aR) stereoisomer of tetrahydrocannabinol; the tetrahydrocannabinol has an absolute configuration set forth by the chemical name (6aR,10aR)-6,6,9-trimethyl-3-pentyl-6a,7,8,10a-tetrahydro-6H-benzo[c]chromen-1-ol; the (6aS,10aR) stereoisomer of tetrahydrocannabinol has an absolute configuration set forth by the chemical name (6aS,10aR)-6,6,9-trimethyl-3-pentyl-6a,7,8,10a-tetrahydro-6H-benzo[c]chromen-1-ol; the heterogeneous composition comprises the tetrahydrocannabinol and the (6aS,10aR) stereoisomer of tetrahydrocannabinol; the alcohol phase comprises at least some of the tetrahydrocannabinol of the starting composition; the alcohol phase comprises at least some of the (6aS,10aR) stereoisomer of tetrahydrocannabinol of the starting composition; the tetrahydrocannabinol of the alcohol phase is a solute that is dissolved in the ethanol of the alcohol phase; the (6aS,10aR) stereoisomer of tetrahydrocannabinol of the alcohol phase is a solute that is dissolved in the ethanol of the alcohol phase; the tetrahydrocannabinol of the starting composition has a solubility in the alcohol phase that is greater than 10 grams per liter; the (6aS,10aR) stereoisomer of tetrahydrocannabinol of the starting composition has a solubility in the alcohol phase that is greater than 10 grams per liter; the tetrahydrocannabinol of the heterogeneous composition has a solubility in the aqueous phase that is less than 10 grams per liter; the (6aS,10aR) stereoisomer of tetrahydrocannabinol of the heterogeneous composition has a solubility in the aqueous phase that is less than 10 grams per liter; the combining of the alcohol phase and the solubility-regulating composition drives a portion of the tetrahydrocannabinol of the alcohol phase out of the alcohol phase; the combining of the alcohol phase and the solubility-regulating composition drives a portion of the (6aS,10aR) stereoisomer of tetrahydrocannabinol of the alcohol phase out of the alcohol phase; the aqueous phase comprises the cannabinoid molecule (or the plurality of cannabinoid molecules) of the aqueous phase, any tetrahydrocannabinol that is dissolved in the solvent of the aqueous phase, and any stereoisomer of (6aS,10aR) tetrahydrocannabinol that is dissolved in the solvent of the aqueous phase at a ratio that is greater than (i) 350 parts by mass of the cannabinoid molecule of the aqueous phase to (ii) 1 part by mass of the sum of (a) any tetrahydrocannabinol that is dissolved in the solvent of the aqueous phase and (b) any (6aS,10aR) stereoisomer of tetrahydrocannabinol that is dissolved in the solvent of the aqueous phase; the lipid phase comprises greater than 50 percent of the tetrahydrocannabinol of the heterogeneous composition; the lipid phase comprises greater than 50 percent of the (6aS,10aR) stereoisomer of tetrahydrocannabinol of the heterogeneous composition; the product comprises the cannabinoid molecule of the product, any tetrahydrocannabinol of the product, and any (6aS,10aR) stereoisomer of tetrahydrocannabinol of the product at a ratio that is greater than (i) 350 parts by mass of the cannabinoid molecule of the product to (ii) 1 part by mass of the sum of (a) any tetrahydrocannabinol of the product and (b) any (6aS,10aR) stereoisomer of tetrahydrocannabinol of the product; the product lacks the tetrahydrocannabinol at a concentration greater than 0.3 percent by mass; and the product lacks the (6aS,10aR) stereoisomer of tetrahydrocannabinol at a concentration greater than 0.2 percent by mass.

In some embodiments, the starting composition comprises limonene; the heterogeneous composition comprises the limonene of the starting composition; the alcohol phase comprises at least some of the limonene of the starting composition; the limonene of the alcohol phase is a solute that is dissolved in the alcohol of the alcohol phase; the limonene of the starting composition has a solubility in the alcohol phase that is greater than 5 grams per liter; the limonene of the heterogeneous composition has a solubility in the aqueous phase that is less than 5 grams per liter; the combining of the alcohol phase and the solubility-regulating composition drives a portion of the limonene of the alcohol phase out of the alcohol phase; the lipid phase comprises greater than 50 percent of the limonene of the heterogeneous composition; and the product lacks limonene at a concentration greater than 0.1 percent by mass.

In some embodiments, the starting composition comprises chlorophyll a; the heterogeneous composition comprises the chlorophyll a of the starting composition; the alcohol phase comprises at least some of the chlorophyll a of the starting composition; the chlorophyll a of the alcohol phase is a solute that is dissolved in the alcohol of the alcohol phase; the chlorophyll a of the starting composition has a solubility in the alcohol phase that is greater than 5 grams per liter; the chlorophyll a of the heterogeneous composition has a solubility in the aqueous phase that is less than 5 grams per liter; the combining of the alcohol phase and the solubility-regulating composition drives a portion of the chlorophyll a of the alcohol phase out of the alcohol phase; the lipid phase comprises greater than 50 percent of the chlorophyll a of the heterogeneous composition; and the product lacks chlorophyll a at a concentration greater than 1 percent by mass.

In some embodiments, the starting composition comprises beta-caryophyllene oxide; the heterogeneous composition comprises the beta-caryophyllene oxide of the starting composition; the alcohol phase comprises at least some of the beta-caryophyllene oxide of the starting composition; the beta-caryophyllene oxide of the alcohol phase is a solute that is dissolved in the alcohol of the alcohol phase; the beta-caryophyllene oxide of the starting composition has a solubility in the alcohol phase that is greater than 5 grams per liter; the beta-caryophyllene oxide of the heterogeneous composition has a solubility in the aqueous phase that is less than 5 grams per liter; the combining of the alcohol phase and the solubility-regulating composition drives a portion of the beta-caryophyllene oxide of the alcohol phase out of the alcohol phase; the lipid phase comprises greater than 50 percent of the beta-caryophyllene oxide of the heterogeneous composition; and the product lacks beta-caryophyllene oxide at a concentration greater than 0.1 percent by mass.

In some embodiments, the starting composition comprises a plurality of second molecules; the plurality of second molecules comprises beta-caryophyllene and beta-caryophyllene oxide; the heterogeneous composition comprises the beta-caryophyllene and the beta-caryophyllene oxide of the starting composition; the alcohol phase comprises at least some of the beta-caryophyllene and the beta-caryophyllene oxide of the starting composition; the beta-caryophyllene and the beta-caryophyllene oxide of the alcohol phase are solutes that are dissolved in the alcohol of the alcohol phase; the beta-caryophyllene of the starting composition has a solubility in the alcohol phase that is greater than 5 grams per liter; the beta-caryophyllene of the heterogeneous composition has a solubility in the aqueous phase that is less than 5 grams per liter; the combining of the alcohol phase and the solubility-regulating composition drives a portion of the beta-caryophyllene of the alcohol phase out of the alcohol phase; the beta-caryophyllene oxide of the starting composition has a solubility in the alcohol phase that is greater than 5 grams per liter; the beta-caryophyllene oxide of the heterogeneous composition has a solubility in the aqueous phase that is less than 5 grams per liter; the combining of the alcohol phase and the solubility-regulating composition drives a portion of the beta-caryophyllene oxide of the alcohol phase out of the alcohol phase; the lipid phase comprises greater than 50 percent of the beta-caryophyllene of the heterogeneous composition; the lipid phase comprises greater than 50 percent of the beta-caryophyllene oxide of the heterogeneous composition; the product lacks beta-caryophyllene at a concentration greater than 0.1 percent by mass; and the product lacks beta-caryophyllene oxide at a concentration greater than 0.1 percent by mass. In some specific embodiments, the starting composition comprises a plurality of second molecules; the plurality of second molecules comprises beta-caryophyllene and beta-caryophyllene oxide; the starting composition comprises the beta-caryophyllene at a concentration of at least 0.05 percent and no greater than 5 percent by mass; the starting composition comprises the beta-caryophyllene oxide at a concentration of at least 0.01 percent and no greater than 1 percent by mass; the starting composition comprises beta-caryophyllene and beta-caryophyllene oxide at a beta-caryophyllene-to-beta-caryophyllene-oxide ratio greater than 5:1 and less than 100:1 by mass; the product lacks the beta-caryophyllene at a concentration greater than 0.05 percent by mass; and the product lacks the beta-caryophyllene oxide at a concentration greater than 0.01 percent by mass.

In some embodiments, the alcohol is ethanol; the solubility-regulating composition comprises a Brønsted acid; decreasing the solubility of the second molecule in the alcohol phase comprises both (i) decreasing the ethoxide anion concentration of the alcohol phase and (ii) increasing the hydrogen cation concentration of the alcohol phase by combining the alcohol phase with the solubility-regulating composition; the aqueous phase of the heterogeneous composition has a hydrogen cation concentration of at least 10 picomolar and no greater than 1 micromolar; the aqueous phase of the heterogeneous composition comprises ethoxide anion and hydroxide anion at a combined concentration of at least 2 nanomolar and no greater than 10 millimolar; combining the alcohol phase and the solubility-regulating composition results in an ethoxide anion concentration of the aqueous phase of the heterogeneous composition that is no greater than half the ethoxide anion concentration of the alcohol phase of the starting composition; the cannabinoid molecule is cannabidiol; the starting composition comprises the cannabidiol of the starting composition as both (i) molecular cannabidiol, which has the chemical name 2-[(1R, 6R)-6-isopropenyl-3-methylcyclohex-2-en-1-yl]-5-pentyl-beneze-1,3-diol and (ii) ionic cannabidiol, which has the chemical name 2-[(1R,6R)-6-isopropenyl-3-methylcyclohex-2-en-1-yl]-3-hydroxy-5-pentylphenolate; the alcohol phase comprises the cannabidiol of the alcohol phase as both molecular cannabidiol and ionic cannabidiol; the molecular cannabidiol of the alcohol phase is a solute that is dissolved in the ethanol of the alcohol phase; the ionic cannabidiol of the alcohol phase is a solute that is dissolved in the ethanol of the alcohol phase; the alcohol phase comprises ionic cannabidiol and molecular cannabidiol at an ionic-cannabidiol-to-molecular-cannabidiol ratio of greater than 100:1 and less than 1,000,000:1; the heterogeneous composition comprises the cannabidiol of the heterogeneous composition as both molecular cannabidiol and ionic cannabidiol; the aqueous phase comprises greater than 80 percent of the ionic cannabidiol of the heterogeneous composition; the ionic cannabidiol of the aqueous phase is a solute that is dissolved in the solvent of the aqueous phase; the aqueous phase comprises molecular cannabidiol; the molecular cannabidiol of the aqueous phase is dissolved in the solute of the aqueous phase; the aqueous phase comprises ionic cannabidiol and molecular cannabidiol at an ionic-cannabidiol-to-molecular-cannabidiol ratio of greater than 1:1 and less than 100:1; the ionic cannabidiol of the heterogeneous composition has a solubility in the aqueous phase that is greater than 10 grams per liter; the molecular cannabidiol of the heterogeneous composition has a solubility in the aqueous phase that is less than 10 grams per liter; the combining of the alcohol phase and the solubility-regulating composition drives a portion of the molecular cannabidiol of the alcohol phase out of the alcohol phase; the lipid phase comprises greater than 50 percent of the molecular cannabidiol of the heterogeneous composition; the separation of (a) the majority of the ethanol of the second fractionated aqueous phase and the majority of the water of the second fractionated aqueous phase from (b) the majority of the cannabidiol of the second fractionated aqueous phase comprises combining the second fractionated aqueous phase and a second solubility-regulating composition to (i) drive a portion of the cannabidiol of the second fractionated aqueous phase out of the second fractionated aqueous phase and (ii) produce a second heterogeneous composition; the second solubility-regulating composition comprises a Brønsted acid; the second heterogeneous composition comprises (a) substantially all of the ethanol of the second fractionated aqueous phase, (b) substantially all of the cannabidiol of the second fractionated aqueous phase, and (c) substantially all of the water of the second fractionated aqueous phase; the second heterogeneous composition comprises a residual aqueous phase and a second enriched lipid phase; the residual aqueous phase is a liquid; the residual aqueous phase comprises greater than 50 percent of the ethanol of the second heterogeneous composition; the residual aqueous phase comprises greater than 95 percent of the water of the second heterogeneous composition; the cannabidiol of the second heterogeneous composition comprises molecular cannabidiol; the Brønsted acid of the second solubility-regulating composition converts a majority of the ionic cannabidiol of the second fractionated aqueous phase into molecular cannabidiol; the molecular cannabidiol of the second heterogeneous composition has a solubility in the residual aqueous phase that is less than 10 grams per liter; the second lipid phase comprises greater than 80 percent of the molecular cannabidiol of the second heterogeneous composition; the separation of (a) the majority of the ethanol of the second fractionated aqueous phase and the majority of the water of the second fractionated aqueous phase from (b) the majority of the cannabidiol of the second fractionated aqueous phase further comprises mechanically separating the residual aqueous phase of the second heterogeneous composition from the second lipid phase of the second heterogeneous composition; and the product consists essentially of the portion of the second lipid phase that is mechanically separated from the residual aqueous phase.

In some embodiments, the alcohol is ethanol; the starting composition has an ethoxide concentration; the aqueous phase has an ethoxide concentration; and combining (a) the starting composition and (b) the solubility-regulating composition decreases the ethoxide concentration of the starting composition to arrive at the ethoxide concentration of the aqueous phase. In some specific embodiments, the alcohol is ethanol; the starting composition has an ethoxide concentration; the aqueous phase has an ethoxide concentration; and combining (a) the starting composition and (b) the solubility-regulating composition decreases the ethoxide concentration of the starting composition to arrive at the ethoxide concentration of the aqueous phase such that the ethoxide concentration of the aqueous phase is at least 0.2 nanomolar less than the ethoxide concentration of the starting composition. In some specific embodiments, the alcohol is ethanol; the starting composition has an ethoxide concentration; the aqueous phase has an ethoxide concentration; and combining (a) the starting composition and (b) the solubility-regulating composition decreases the ethoxide concentration of the starting composition to arrive at the ethoxide concentration such that the ethoxide concentration of the aqueous phase is less than 95 percent of the ethoxide concentration of the starting composition. For example, the starting composition may have an ethoxide concentration of about 50 nanomolar, and the aqueous phase may have an ethoxide concentration of about 40 nanomolar, which is both at least 0.2 nanomolar less than the ethoxide concentration of the starting composition and less than 95 percent of the ethoxide concentration of the starting composition.

Various combinations of the features disclosed in this patent document will be evident to those of ordinary skill, and these combinations are expressly contemplated. This patent document discloses each linguistic and grammatical combination of different features disclosed anywhere in the patent document as though any specific combination were disclosed in the same sentence. The language and grammar of this patent document are intentionally selected to explicitly clarify the combinations contemplated such that, for example, methods that feature either the genus "alcohol" or the species "ethanol" are combinable with "ethoxide" embodiments.

The words "comprising," "comprises," and "comprise" refer to open-ended sets. For example, a composition comprising an alcohol phase can also comprise a lipid phase.

The phrases "consisting of," "consists of," and "consist of" refer to closed sets. For example, a product that consists of a portion of an aqueous phase that is not both vaporized and removed from the aqueous phase cannot also comprise any molecule that is both vaporized and removed, although the product may comprise a molecule of the type that is both vaporized and removed, for example, when a separation is an incomplete separation.

Each instance of the words "comprising," "comprises," and "comprise" in this patent document may be substituted with the phrases "consisting of," "consists of," and "consist of," respectively.

The phrases "consisting essentially of," "consists essentially of," and "consist essentially of" refer to closed sets that optionally contain one or more undisclosed elements that do not materially affect the nature of any given closed set. For example, a product that consists essentially of a portion of a cannabidiol-enriched lipid phase that is mechanically separated from a residual aqueous phase can nevertheless comprise an amount of the residual aqueous phase such as either (i) a trace amount, (ii) a fractional amount that cannot be removed in a viable commercial embodiment, or (iii) an amount that an unscrupulous patent infringer may intentionally include in an attempt to avoid a patent claim that matures from this patent document while performing a method that would otherwise infringe the patent claim.

Each instance of the words "comprising," "comprises," and "comprise" in this patent document may be substituted with the phrases "consisting essentially of," "consists essentially of," and "consist essentially of," respectively.

Each instance of the phrases "consisting of," "consists of," and "consist of" in this patent document may be substituted with the phrases "consisting essentially of," "consists essentially of," and "consist essentially of," respectively.

The word "any" as used to refer to a molecule that may be present in either a composition or a phase of a composition, such as "any water that is present in the alcohol phase," refers to an amount of the molecule that includes zero, an infinitesimally small amount, an undetectable amount, and a trace amount. For example, the phrase, "any tetrahydrocannabinol that is dissolved in the solvent of the aqueous phase," contemplates that each of: (a) a measurable, non-zero amount of tetrahydrocannabinol is dissolved in the solvent of the aqueous phase, (b) a trace amount of tetrahydrocannabinol is dissolved in the solvent of the aqueous phase, (c) no detectable tetrahydrocannabinol is dissolved in the solvent of the aqueous phase, (d) an infinitesimally small amount of tetrahydrocannabinol is dissolved in the solvent of the aqueous phase, and (e) zero tetrahydrocannabinol is dissolved in the solvent of the aqueous phase.

The following examples provide a framework to implement certain aspects of the disclosure, and these examples do not limit the scope of this patent document or any claim that matures from the disclosure of this patent document.

Example 1. Separation of a Cannabinoid Molecule and a Second Molecule by Diluting an Alcohol Solution with Water to Adjust the Solubility of the Second Molecule 0.5 grams of a cannabinoid molecule (cannabidiol) was dissolved in 3.3 milliliters of an alcohol phase that consisted of 0.5 molar potassium hydroxide in ethanol to provide a starting composition.

The starting composition consisted of an alcohol (ethanol), a cannabinoid molecule (cannabidiol), and a second molecule (hydrophobic impurities). The starting composition consisted of an alcohol phase. The alcohol phase was a liquid phase. The alcohol phase comprised (a) substantially all of the alcohol of the starting composition, (b) substantially all of the cannabinoid molecule of the starting composition, and (c) substantially all of the second molecule of the starting composition. The alcohol of the alcohol phase was a solvent. The cannabinoid molecule of the alcohol phase was a solute that was dissolved in the alcohol of the alcohol phase. The second molecule of the alcohol phase was a solute that was dissolved in the alcohol of the alcohol phase. The alcohol of the alcohol phase was present in the alcohol phase at a concentration of approximately 81 percent by mass. The starting composition comprised the cannabinoid molecule at a concentration of approximately 16 percent by mass. The starting composition comprised the second molecule at an unknown concentration that was no greater than 6.5 percent by mass. The starting composition comprised the cannabinoid molecule and the second molecule at an unknown ratio that was greater than 10:1. The alcohol phase comprised ethoxide anion at a concentration of approximately 18 millimolar. The cannabinoid molecule of the starting composition had a solubility in the alcohol phase that was greater than 10 grams per liter. The second molecule of the starting composition had a solubility in the alcohol phase that was greater than 10 grams per liter.

The solubility of the second molecule in the alcohol phase of the starting composition was decreased by combining the alcohol phase and a solubility-regulating composition to (a) drive a portion of the second molecule of the alcohol phase out of the alcohol phase and (b) produce a heterogeneous composition. The solubility-regulating composition comprised water. Specifically, the solubility-regulating composition was 26.7 milliliters of 0.1 molar sodium carbonate. A 10 milliliter aliquot was taken from the heterogeneous composition. The heterogeneous composition comprised solutes in the following approximate amounts:

| | |
|---|---|
| 167 milligrams ionic cannabidiol | 53 milligrams carbonate |
| 21 milligrams potassium | 868 milligrams ethanol |
| 41 milligrams sodium | 8.8 grams water |

The solubility-regulating composition comprised the water at a concentration by mass that was greater than the concentration by mass of any water that was present in the alcohol phase of the starting composition such that the combination of the alcohol phase and the solubility-regulating composition had a greater concentration of water than the alcohol phase of the starting composition.

The heterogeneous composition comprised each of (a) the alcohol of the starting composition, (b) the cannabinoid molecule of the starting composition, (c) the second molecule of the starting composition, and (d) the water of the solubility-regulating composition. The heterogeneous composition comprised an aqueous phase and a lipid phase. The aqueous phase was a liquid. The aqueous phase comprised greater than 50 percent of the cannabinoid molecule of the heterogeneous composition. The aqueous phase comprised substantially all of the alcohol of the heterogeneous composition. The aqueous phase comprised substantially all of the water of the heterogeneous composition. The water of the aqueous phase was a solvent, and the ethanol of the aqueous phase was a cosolvent. The cannabinoid molecule of the heterogeneous composition had a solubility in the aqueous phase that was greater than 10 grams per liter. The cannabinoid molecule of the aqueous phase was a solute that was dissolved in the solvent of the aqueous phase. The second molecule of the heterogeneous composition had a solubility in the aqueous phase that was less than 10 grams per liter. The aqueous phase comprised the cannabinoid molecule of the aqueous phase and any second molecule that was dissolved in the solvent of the aqueous phase at a cannabinoid-molecule-to-second-molecule ratio that was greater than 350:1 by mass. The lipid phase comprised greater than 50 percent of the second molecule of the heterogeneous composition.

The entire heterogeneous composition could fit into a single 15 milliliter centrifuge tube, and so all of the heterogeneous composition was selected for further processing to produce a fractionated heterogeneous composition. The fractionated heterogeneous composition comprised a fractionated aqueous phase and a fractionated lipid phase. The fractionated aqueous phase consisted of all of the aqueous phase of the heterogeneous composition. The fractionated aqueous phase comprised all of the cannabinoid molecule of the aqueous phase. The fractionated aqueous phase comprised all of the alcohol of the aqueous phase. The fractionated aqueous phase comprised all of the water of the aqueous phase. The fractionated lipid phase consisted of all of the lipid phase of the heterogeneous composition. The fractionated lipid phase comprised all of the second molecule of the lipid phase of the heterogeneous composition.

The fractionated aqueous phase of the fractionated heterogeneous composition was mechanically separated from the fractionated lipid phase of the fractionated heterogeneous composition to mechanically separate the cannabinoid molecule of the fractionated aqueous phase from the second molecule of the fractionated lipid phase. The mechanical separation of the fractionated aqueous phase of the fractionated heterogeneous composition from the fractionated lipid phase of the fractionated heterogeneous composition comprised centrifuging the fractionated heterogeneous composition.

All of the fractionated aqueous phase was selected for further processing to produce a second fractionated aqueous phase. The second fractionated aqueous phase comprised all of the cannabinoid molecule of the fractionated aqueous phase. The second fractionated aqueous phase comprised all of the alcohol of the fractionated aqueous phase. The second fractionated aqueous phase comprised all of the water of the fractionated aqueous phase.

The majority of the alcohol of the second fractionated aqueous phase and the majority of the water of the second fractionated aqueous phase were then separated from the majority of the cannabinoid molecule of the second fractionated aqueous phase to produce a product.

The separation of (a) the majority of the alcohol of the second fractionated aqueous phase and the majority of the water of the second fractionated aqueous phase from (b) the majority of the cannabinoid molecule of the second fractionated aqueous phase comprised combining the second fractionated aqueous phase and a second solubility-regulating composition to (i) drive a portion of the cannabinoid molecule of the second fractionated aqueous phase out of the second fractionated aqueous phase and (ii) produce a second heterogeneous composition. The second solubility-regulating composition comprised a Brønsted acid. Specifically, the second solubility-regulating composition was 0.1 milliliters of 5 molar citric acid.

The second heterogeneous composition comprised (a) substantially all of the alcohol of the second fractionated aqueous phase, (b) substantially all of the cannabinoid molecule of the second fractionated aqueous phase, and (c)

substantially all of the water of the second fractionated aqueous phase. The second heterogeneous composition comprised a residual aqueous phase and a second lipid phase. The residual aqueous phase was a liquid. The residual aqueous phase comprised substantially all of the alcohol of the second heterogeneous composition. The residual aqueous phase comprised substantially all of the water of the second heterogeneous composition. The cannabinoid molecule of the second heterogeneous composition was molecular cannabidiol. The Brønsted acid of the second solubility-regulating composition converted a majority of the ionic cannabinoid molecule of the second fractionated aqueous phase into the molecular form of the cannabinoid molecule in the second heterogeneous composition. The molecular cannabinoid molecule of the second heterogeneous composition had a solubility in the residual aqueous phase that was less than 10 grams per liter. The second lipid phase comprised greater than 80 percent of the molecular cannabinoid molecule of the second heterogeneous composition.

The separation of (a) the majority of the alcohol of the second fractionated aqueous phase and the majority of the water of the second fractionated aqueous phase from (b) the majority of the cannabinoid molecule of the second fractionated aqueous phase further comprised mechanically separating the residual aqueous phase of the second heterogeneous composition from the second enriched lipid phase of the second heterogeneous composition. The mechanical separation of the residual aqueous phase of the second heterogeneous composition from the lipid phase of the second heterogeneous composition comprised centrifuging the second heterogeneous composition to produce (a) an aqueous liquid, which comprised the majority of the alcohol of the second fractionated aqueous phase and the majority of the water of the second fractionated aqueous phase, and (b) an oil and any precipitate, which comprised the majority of the cannabidiol of the second fractionated aqueous phase.

The product consisted essentially of the oil and any precipitate, which consisted essentially of the portion of the lipid phase that was mechanically separated from the residual aqueous phase. The product was obtained at a temperature of about 21 degrees Celsius. The oil was a supercooled liquid. The temperature of the product was below the freezing point of the oil.

The product comprised the cannabinoid molecule. The product lacked the second molecule at a concentration greater than 0.3 percent by mass. The product lacked tetrahydrocannabinol at a concentration greater than 0.3 percent by mass. The product comprised cannabidiol and any tetrahydrocannabinol at a cannabidiol-to-tetrahydrocannabinol ratio that was greater that 350:1 by mass. The product lacked cannabichromene at a concentration greater than 5 percent by mass. The product lacked beta-caryophyllene at a concentration greater than 5 percent by mass. The product lacked beta-caryophyllene oxide at a concentration greater than 0.1 percent by mass. The product lacked limonene at a concentration greater than 0.1 percent by mass. The product lacked chlorophyll a at a concentration greater than 1 percent by mass. The product lacked (6aS,10aR)-6,6,9-trimethyl-3-pentyl-6a,7,8,10a-tetrahydro-6H-benzo[c]chromen-1-ol at a concentration greater than 0.2 percent by mass. The product lacked any alcohol at a concentration greater than 5 percent by mass. The product lacked water at a concentration greater than 5 percent by mass.

Example 2. Separation of a Plurality of Cannabinoid Molecules from a Plurality of Second Molecules Example 1 is repeated by replacing the 0.5 grams of cannabidiol with 0.5 grams of decarboxylated industrial hemp extract containing 0.3 grams of cannabidiol, 0.02 grams of tetrahydrocannabinol, 0.01 grams of (6aS,10aR) stereoisomer of tetrahydrocannabinol, 0.02 grams of cannabichromene, 0.01 grams of cannabigerol, 0.02 grams of beta-caryophyllene, 0.001 grams of beta-caryophyllene oxide, and 0.005 grams of limonene. The method separates a plurality of cannabinoid molecules that include the cannabidiol and cannabigerol from a plurality of second molecules that include the tetrahydrocannabinol, (6aS,10aR) stereoisomer of tetrahydrocannabinol, cannabichromene, beta-caryophyllene, beta-caryophyllene oxide, and limonene.

What is claimed is:

1. A method to separate cannabidiol and tetrahydrocannabinol, comprising:
(i) providing a starting composition comprising ethanol, cannabidiol, and tetrahydrocannabinol, in which:
   the starting composition comprises an alcohol phase;
   the alcohol phase is a liquid;
   the alcohol phase comprises (a) at least 90 percent of the ethanol of the starting composition, (b) at least 50 percent of the cannabidiol of the starting composition, and (c) at least some of the tetrahydrocannabinol of the starting composition;
   the ethanol of the alcohol phase is a solvent;
   the cannabidiol of the alcohol phase is a solute that is dissolved in the ethanol of the alcohol phase;
   the tetrahydrocannabinol of the alcohol phase is a solute that is dissolved in the ethanol of the alcohol phase;
   the ethanol of the alcohol phase is present in the alcohol phase at a concentration of at least 35 percent and no greater than 99 percent by mass;
   the starting composition comprises the cannabidiol at a concentration of at least 0.65 percent and no greater than 65 percent by mass;
   the starting composition comprises the tetrahydrocannabinol at a concentration of at least 0.065 percent and no greater than 6.5 percent by mass;
   the starting composition comprises the cannabidiol and the tetrahydrocannabinol at a cannabidiol-to-tetrahydrocannabinol ratio of at least 10:1 and less than 350:1 by mass;
   the cannabidiol of the starting composition has a solubility in the alcohol phase that is greater than 10 grams per liter; and
   the tetrahydrocannabinol of the starting composition has a solubility in the alcohol phase that is greater than 10 grams per liter;
(ii) decreasing the solubility of the tetrahydrocannabinol in the alcohol phase of the starting composition by combining the alcohol phase and a solubility-regulating composition to (a) drive a portion of the tetrahydrocannabinol of the alcohol phase out of the alcohol phase and (b) produce a heterogeneous composition, in which:
   the solubility-regulating composition comprises water;
   the solubility-regulating composition comprises the water at a concentration by mass that is greater than the concentration by mass of any water that is present in the alcohol phase of the starting composition such that the combination of the alcohol phase and the solubility-regulating composition has a greater concentration of water than the alcohol phase of the starting composition;
   the heterogeneous composition comprises each of (a) the ethanol of the starting composition, (b) the cannabidiol of the starting composition, (c) the tetrahydrocannabinol of the starting composition, and (d) the water of the solubility-regulating composition;

the heterogeneous composition comprises an aqueous phase and a tetrahydrocannabinol-enriched lipid phase;

the aqueous phase is a liquid;

the aqueous phase comprises greater than 50 percent of the cannabidiol of the heterogeneous composition;

the aqueous phase comprises greater than 50 percent of the ethanol of the heterogeneous composition;

the aqueous phase comprises at least 95 percent of the water of the heterogeneous composition;

either (a) the ethanol of the aqueous phase is a solvent, and the water of the aqueous phase is a solute that is dissolved in the ethanol of the aqueous phase, or (b) the water of the aqueous phase is a solvent, and the ethanol of the aqueous phase is a cosolvent;

the cannabidiol of the heterogeneous composition has a solubility in the aqueous phase that is greater than 10 grams per liter;

the cannabidiol of the aqueous phase is a solute that is dissolved in the solvent of the aqueous phase;

the tetrahydrocannabinol of the heterogeneous composition has a solubility in the aqueous phase that is less than 10 grams per liter;

the aqueous phase comprises the cannabidiol of the aqueous phase and any tetrahydrocannabinol that is dissolved in the solvent of the aqueous phase at a cannabidiol-to-tetrahydrocannabinol ratio that is greater than 350:1 by mass; and the tetrahydrocannabinol-enriched lipid phase comprises greater than 50 percent of the tetrahydrocannabinol of the heterogeneous composition;

(iii) selecting either a fraction or all of the heterogeneous composition for further processing to produce a fractionated heterogeneous composition, in which:

the fractionated heterogeneous composition comprises a fractionated aqueous phase and a fractionated tetrahydrocannabinol-enriched lipid phase;

the fractionated aqueous phase consists of either a fraction or all of the aqueous phase of the heterogeneous composition;

the fractionated aqueous phase comprises either a fraction or all of the cannabidiol of the aqueous phase;

the fractionated aqueous phase comprises either a fraction or all of the ethanol of the aqueous phase;

the fractionated aqueous phase comprises either a fraction or all of the water of the aqueous phase;

the fractionated tetrahydrocannabinol-enriched lipid phase consists of either a fraction or all of the tetrahydrocannabinol-enriched lipid phase of the heterogeneous composition; and the fractionated tetrahydrocannabinol-enriched lipid phase comprises either a fraction or all of the tetrahydrocannabinol of the tetrahydrocannabinol-enriched lipid phase of the heterogeneous composition;

(iv) mechanically separating the fractionated aqueous phase of the fractionated heterogeneous composition from the fractionated tetrahydrocannabinol-enriched lipid phase of the fractionated heterogeneous composition to mechanically separate the cannabidiol of the fractionated aqueous phase from the tetrahydrocannabinol of the fractionated tetrahydrocannabinol-enriched lipid phase;

(v) selecting either a fraction or all of the fractionated aqueous phase for further processing to produce a second fractionated aqueous phase, in which:

the second fractionated aqueous phase comprises either a fraction or all of the cannabidiol of the fractionated aqueous phase;

the second fractionated aqueous phase comprises either a fraction or all of the ethanol of the fractionated aqueous phase; and the second fractionated aqueous phase comprises either a fraction or all of the water of the fractionated aqueous phase;

(vi) separating (a) a majority of the ethanol of the second fractionated aqueous phase and a majority of the water of the second fractionated aqueous phase from (b) a majority of the cannabidiol of the second fractionated aqueous phase to produce a product, in which:

the product comprises cannabidiol;

the product lacks tetrahydrocannabinol at a concentration greater than 0.3 percent by mass;

the product comprises cannabidiol and any tetrahydrocannabinol at a cannabidiol-to-tetrahydrocannabinol ratio that is greater that 350:1 by mass;

the product lacks ethanol at a concentration greater than 5 percent by mass; and the product lacks water at a concentration greater than 5 percent by mass.

2. The method of claim 1, in which:

the starting composition comprises ethanol at a concentration of 35 percent to 90 percent by mass;

the starting composition comprises cannabidiol at a concentration of 5 percent to 60 percent by mass;

the starting composition comprises tetrahydrocannabinol at a concentration of to 0.1 percent to 5 percent by mass;

the starting composition comprises cannabichromene at a concentration of 0.1 percent to 5 percent by mass;

the starting composition comprises cannabigerol at a concentration of 0.05 percent to 3 percent by mass;

the starting composition comprises beta-caryophyllene at a concentration of 0.1 percent to 5 percent by mass;

the alcohol phase comprises (a) at least some of the cannabichromene of the starting composition, (b) at least some of the cannabigerol of the starting composition, and (c) at least some of the beta-caryophyllene of the starting composition;

the cannabichromene of the alcohol phase is a solute that is dissolved in the ethanol of the alcohol phase;

the cannabigerol of the alcohol phase is a solute that is dissolved in the ethanol of the alcohol phase;

the beta-caryophyllene of the alcohol phase is a solute that is dissolved in the ethanol of the alcohol phase;

the heterogeneous composition comprises each of (a) the cannabichromene of the starting composition, (b) the cannabigerol of the starting composition, and (c) the beta-caryophyllene of the starting composition;

the cannabichromene of the starting composition has a solubility in the alcohol phase that is greater than 10 grams per liter;

the cannabichromene of the heterogeneous composition has a solubility in the aqueous phase that is less than 10 grams per liter;

the combining of the alcohol phase and the solubility-regulating composition drives a portion of the cannabichromene of the alcohol phase out of the alcohol phase;

the beta-caryophyllene of the starting composition has a solubility in the alcohol phase that is greater than 5 grams per liter;

the beta-caryophyllene of the heterogeneous composition has a solubility in the aqueous phase that is less than 5 grams per liter;

the combining of the alcohol phase and the solubility-regulating composition drives a portion of the beta-caryophyllene of the alcohol phase out of the alcohol phase;

the cannabigerol of the starting composition has a solubility in the alcohol phase that is greater than 10 grams per liter;

the cannabigerol of the heterogeneous composition has a solubility in the aqueous phase that is greater than 10 grams per liter;

the aqueous phase comprises greater than 65 percent of the cannabigerol of the heterogeneous composition;

the cannabigerol of the aqueous phase is a solute that is dissolved in the solvent of the aqueous phase;

the aqueous phase comprises greater than 65 percent of the cannabidiol of the heterogeneous composition;

the tetrahydrocannabinol-enriched lipid phase comprises greater than 65 percent of the tetrahydrocannabinol of the heterogeneous composition;

the tetrahydrocannabinol-enriched lipid phase comprises greater than 65 percent of the cannabichromene of the heterogeneous composition;

the tetrahydrocannabinol-enriched lipid phase comprises greater than 65 percent of the beta-caryophyllene of the heterogeneous composition;

the mechanical separation of the fractionated aqueous phase of the fractionated heterogeneous composition from the fractionated tetrahydrocannabinol-enriched lipid phase of the fractionated heterogeneous composition comprises centrifuging the fractionated heterogeneous composition;

the separation of (a) the majority of the ethanol of the second fractionated aqueous phase and the majority of the water of the second fractionated aqueous phase from (b) the majority of the cannabidiol of the second fractionated aqueous phase comprises combining the second fractionated aqueous phase and a second solubility-regulating composition to (i) drive a portion of the cannabidiol of the second fractionated aqueous phase out of the second fractionated aqueous phase, (ii) drive a portion of the cannabigerol of the second fractionated aqueous phase out of the second fractionated aqueous phase, and (iii) produce a second heterogeneous composition;

the second solubility-regulating composition comprises water at a concentration by mass that is greater than the concentration by mass of the water that is present in the second fractionated aqueous phase such that the combination of the second fractionated aqueous phase and the second solubility-regulating composition has a greater concentration of water than the second fractionated aqueous phase;

the second heterogeneous composition comprises (a) substantially all of the ethanol of the second fractionated aqueous phase, (b) substantially all of the cannabidiol of the second fractionated aqueous phase, (c) substantially all of the cannabigerol of the second fractionated aqueous phase, (d) substantially all of the water of the second fractionated aqueous phase, and (e) the water of the second solubility-regulating composition;

the second heterogeneous composition comprises a residual aqueous phase and a cannabidiol-enriched lipid phase;

the residual aqueous phase is a liquid;

the residual aqueous phase comprises greater than 50 percent of the ethanol of the second heterogeneous composition;

the residual aqueous phase comprises greater than 95 percent of the water of the second heterogeneous composition;

the cannabidiol of the second heterogeneous composition has a solubility in the residual aqueous phase that is less than 10 grams per liter;

the cannabidiol-enriched lipid phase comprises greater than 80 percent of the cannabidiol of the second heterogeneous composition;

the cannabigerol of the second heterogeneous composition has a solubility in the residual aqueous phase that is less than 10 grams per liter;

the cannabidiol-enriched lipid phase comprises greater than 80 percent of the cannabigerol of the second heterogeneous composition;

the cannabidiol-enriched lipid phase comprises the cannabidiol of the cannabidiol-enriched lipid phase and any tetrahydrocannabinol that is present in the cannabidiol-enriched lipid phase at a cannabidiol-to-tetrahydrocannabinol ratio that is greater than 350:1 by mass;

the separation of (a) the majority of the ethanol of the second fractionated aqueous phase and the majority of the water of the second fractionated aqueous phase from (b) the majority of the cannabidiol of the second fractionated aqueous phase further comprises mechanically separating the residual aqueous phase of the second heterogeneous composition from the cannabidiol-enriched lipid phase of the second heterogeneous composition;

the mechanical separation of the residual aqueous phase of the second heterogeneous composition from the cannabidiol-enriched lipid phase of the second heterogeneous composition comprises centrifuging the second heterogeneous composition to produce (a) an aqueous liquid, which comprises the majority of the ethanol of the second fractionated aqueous phase and the majority of the water of the second fractionated aqueous phase, and (b) an oil and any precipitate, which comprises the majority of the cannabidiol of the second fractionated aqueous phase;

the product consists essentially of the oil and any precipitate;

the product comprises cannabidiol at a concentration of at least 75 percent by mass;

the product comprises cannabigerol at a concentration of at least 0.05 percent and no greater than 5 percent by mass;

the product lacks cannabichromene at a concentration greater than 5 percent by mass;

the product lacks beta-caryophyllene at a concentration greater than 5 percent by mass;

the product is obtained at a temperature of at least 20 degrees Celsius and no greater than 65 degrees Celsius;

the oil is a supercooled liquid; and the temperature of the product is below the freezing point of the oil.

3. The method of claim 1, in which the starting composition comprises:

ethanol at a concentration of 35 percent to 90 percent by mass;

cannabidiol at a concentration of 5 percent to 60 percent by mass; and tetrahydrocannabinol at a concentration of to 0.1 percent to 5 percent by mass.

4. The method of claim 3, in which:
the starting composition comprises cannabichromene, cannabigerol, and beta-caryophyllene;
the alcohol phase comprises (a) at least some of the cannabichromene of the starting composition, (b) at least some of the cannabigerol of the starting composition, and (c) at least some of the beta-caryophyllene of the starting composition;
the cannabichromene of the alcohol phase is a solute that is dissolved in the ethanol of the alcohol phase;
the cannabigerol of the alcohol phase is a solute that is dissolved in the ethanol of the alcohol phase;
the beta-caryophyllene of the alcohol phase is a solute that is dissolved in the ethanol of the alcohol phase;
the combining of the alcohol phase and the solubility-regulating composition drives a portion of the cannabichromene of the alcohol phase out of the alcohol phase;
the combining of the alcohol phase and the solubility-regulating composition drives a portion of the beta-caryophyllene of the alcohol phase out of the alcohol phase;
the heterogeneous composition comprises each of (a) the cannabichromene of the starting composition, (b) the cannabigerol of the starting composition, and (c) the beta-caryophyllene of the starting composition;
the aqueous phase comprises greater than 65 percent of the cannabigerol of the heterogeneous composition;
the cannabigerol of the aqueous phase is a solute that is dissolved in the solvent of the aqueous phase;
the aqueous phase comprises greater than 65 percent of the cannabidiol of the heterogeneous composition;
the tetrahydrocannabinol-enriched lipid phase comprises greater than 65 percent of the tetrahydrocannabinol of the heterogeneous composition;
the tetrahydrocannabinol-enriched lipid phase comprises greater than 65 percent of the cannabichromene of the heterogeneous composition;
the tetrahydrocannabinol-enriched lipid phase comprises greater than 65 percent of the beta-caryophyllene of the heterogeneous composition;
the product comprises cannabigerol;
the product lacks cannabichromene at a concentration greater than 5 percent by mass; and
the product lacks beta-caryophyllene at a concentration greater than 5 percent by mass.

5. The method of claim 4, in which:
the tetrahydrocannabinol has an absolute configuration set forth by the chemical name (6aR,10aR)-6,6,9-trimethyl-3-pentyl-6a,7,8,10a-tetrahydro-6H-benzo[c]chromen-1-ol;
the starting composition comprises a stereoisomer of tetrahydrocannabinol that has an absolute configuration set forth by the chemical name (6aS,10aR)-6,6,9-trimethyl-3-pentyl-6a,7,8,10a-tetrahydro-6H-benzo[c]chromen-1-ol;
the heterogeneous composition comprises the stereoisomer of tetrahydrocannabinol;
the alcohol phase comprises at least some of the stereoisomer of tetrahydrocannabinol of the starting composition;
the stereoisomer of tetrahydrocannabinol of the alcohol phase is a solute that is dissolved in the ethanol of the alcohol phase;
the stereoisomer of tetrahydrocannabinol of the starting composition has a solubility in the alcohol phase that is greater than 10 grams per liter;
the stereoisomer of tetrahydrocannabinol of the heterogeneous composition has a solubility in the aqueous phase that is less than 10 grams per liter;
the combining of the alcohol phase and the solubility-regulating composition drives a portion of the stereoisomer of tetrahydrocannabinol of the alcohol phase out of the alcohol phase;
the aqueous phase comprises the cannabidiol of the aqueous phase, any tetrahydrocannabinol that is dissolved in the solvent of the aqueous phase, and any stereoisomer of tetrahydrocannabinol that is dissolved in the solvent of the aqueous phase at a ratio that is greater than (i) 350 parts by mass cannabidiol of the aqueous phase to (ii) 1 part by mass of the sum of (a) any tetrahydrocannabinol that is dissolved in the solvent of the aqueous phase and (b) any stereoisomer of tetrahydrocannabinol that is dissolved in the solvent of the aqueous phase;
the tetrahydrocannabinol-enriched lipid phase comprises greater than 50 percent of the stereoisomer of tetrahydrocannabinol of the heterogeneous composition;
the product comprises the cannabidiol of the product, any tetrahydrocannabinol of the product, and any stereoisomer of tetrahydrocannabinol of the product at a ratio that is greater than (i) 350 parts by mass cannabidiol of the product to (ii) 1 part by mass of the sum of (a) any tetrahydrocannabinol of the product and (b) any stereoisomer of tetrahydrocannabinol of the product; and
the product lacks the stereoisomer of tetrahydrocannabinol at a concentration greater than 0.2 percent by mass.

6. The method of claim 4, in which
the starting composition comprises limonene;
the heterogeneous composition comprises the limonene of the starting composition;
the alcohol phase comprises at least some of the limonene of the starting composition;
the limonene of the alcohol phase is a solute that is dissolved in the ethanol of the alcohol phase;
the limonene of the starting composition has a solubility in the alcohol phase that is greater than 5 grams per liter;
the limonene of the heterogeneous composition has a solubility in the aqueous phase that is less than 5 grams per liter;
the combining of the alcohol phase and the solubility-regulating composition drives a portion of the limonene of the alcohol phase out of the alcohol phase;
the tetrahydrocannabinol-enriched lipid phase comprises greater than 50 percent of the limonene of the heterogeneous composition; and
the product lacks limonene at a concentration greater than 0.1 percent by mass.

7. The method of claim 4, in which
the starting composition comprises chlorophyll a;
the heterogeneous composition comprises the chlorophyll a of the starting composition;
the alcohol phase comprises at least some of the chlorophyll a of the starting composition;
the chlorophyll a of the alcohol phase is a solute that is dissolved in the ethanol of the alcohol phase;
the chlorophyll a of the starting composition has a solubility in the alcohol phase that is greater than 5 grams per liter;
the chlorophyll a of the heterogeneous composition has a solubility in the aqueous phase that is less than 5 grams per liter;

combining the alcohol phase and the solubility-regulating composition drives a portion of the chlorophyll a of the alcohol phase out of the alcohol phase;

the tetrahydrocannabinol-enriched lipid phase comprises greater than 50 percent of the chlorophyll a of the heterogeneous composition; and the product lacks chlorophyll a at a concentration greater than 1 percent by mass.

8. The method of claim 4, in which:

the starting composition comprises beta-caryophyllene oxide;

the heterogeneous composition comprises the beta-caryophyllene oxide of the starting composition;

the alcohol phase comprises at least some of the beta-caryophyllene oxide of the starting composition;

the beta-caryophyllene oxide of the alcohol phase is a solute that is dissolved in the ethanol of the alcohol phase;

the beta-caryophyllene oxide of the starting composition has a solubility in the alcohol phase that is greater than 5 grams per liter;

the beta-caryophyllene oxide of the heterogeneous composition has a solubility in the aqueous phase that is less than 5 grams per liter;

combining the alcohol phase and the solubility-regulating composition drives a portion of the beta-caryophyllene oxide of the alcohol phase out of the alcohol phase;

the tetrahydrocannabinol-enriched lipid phase comprises greater than 50 percent of the beta-caryophyllene oxide of the heterogeneous composition; and the product lacks beta-caryophyllene oxide at a concentration greater than 0.1 percent by mass.

9. The method of claim 8, in which:

the starting composition comprises the beta-caryophyllene at a concentration of at least 0.05 percent and no greater than 5 percent by mass;

the starting composition comprises the beta-caryophyllene oxide at a concentration of at least 0.01 percent and no greater than 1 percent by mass;

the starting composition comprises beta-caryophyllene and beta-caryophyllene oxide at a beta-caryophyllene-to-beta-caryophyllene-oxide ratio greater than 5:1 and less than 100:1 by mass;

the product lacks the beta-caryophyllene at a concentration greater than 0.05 percent by mass; and the product lacks the beta-caryophyllene oxide at a concentration greater than 0.01 percent by mass.

10. The method of claim 1, in which:

the alcohol phase comprises hydrogen cation at a concentration of at least 1 femtomolar and no greater than 500 micromolar;

the alcohol phase comprises ethoxide anion at a concentration of at least 2 picomolar and no greater than 2 molar;

the aqueous phase of the heterogeneous composition has a hydrogen cation concentration of at least 10 picomolar and no greater than 1 micromolar;

the aqueous phase of the heterogeneous composition comprises ethoxide anion and hydroxide anion at a combined concentration of at least 2 nanomolar and no greater than 10 millimolar; and combining the alcohol phase and the solubility-regulating composition results in an ethoxide anion concentration of the aqueous phase of the heterogeneous composition that is no greater than half the ethoxide anion concentration of the alcohol phase of the starting composition.

11. The method of claim 10, in which:

the solubility-regulating composition comprises a Brønsted acid;

decreasing the solubility of the tetrahydrocannabinol in the alcohol phase comprises both (i) decreasing the ethoxide anion concentration of the alcohol phase and (ii) increasing the hydrogen cation concentration of the alcohol phase by combining the alcohol phase with the solubility-regulating composition;

the starting composition comprises the cannabidiol of the starting composition as both (i) molecular cannabidiol, which has the chemical name 2-[(1R,6R)-6-isopropenyl-3-methylcyclohex-2-en-1-yl]-5-pentylbeneze-1,3-diol and (ii) ionic cannabidiol, which has the chemical name 2-[(1R,6R)-6-isopropenyl-3-methylcyclohex-2-en-1-yl]-3-hydroxy-5-pentylphenolate;

the alcohol phase comprises the cannabidiol of the alcohol phase as both molecular cannabidiol and ionic cannabidiol;

the molecular cannabidiol of the alcohol phase is a solute that is dissolved in the ethanol of the alcohol phase;

the ionic cannabidiol of the alcohol phase is a solute that is dissolved in the ethanol of the alcohol phase;

the alcohol phase comprises ionic cannabidiol and molecular cannabidiol at an ionic-cannabidiol-to-molecular-cannabidiol ratio of greater than 100:1 and less than 1,000,000:1;

the heterogeneous composition comprises the cannabidiol of the heterogeneous composition as both molecular cannabidiol and ionic cannabidiol;

the aqueous phase comprises greater than 80 percent of the ionic cannabidiol of the heterogeneous composition;

the ionic cannabidiol of the aqueous phase is a solute that is dissolved in the solvent of the aqueous phase;

the aqueous phase comprises molecular cannabidiol;

the molecular cannabidiol of the aqueous phase is dissolved in the solute of the aqueous phase;

the aqueous phase comprises ionic cannabidiol and molecular cannabidiol at an ionic-cannabidiol-to-molecular-cannabidiol ratio of greater than 1:1 and less than 100:1;

the ionic cannabidiol of the heterogeneous composition has a solubility in the aqueous phase that is greater than 10 grams per liter;

the molecular cannabidiol of the heterogeneous composition has a solubility in the aqueous phase that is less than 10 grams per liter;

the combining of the alcohol phase and the solubility-regulating composition drives a portion of the molecular cannabidiol of the alcohol phase out of the alcohol phase;

the tetrahydrocannabinol-enriched lipid phase comprises greater than 50 percent of the molecular cannabidiol of the heterogeneous composition;

the separation of (a) the majority of the ethanol of the second fractionated aqueous phase and the majority of the water of the second fractionated aqueous phase from (b) the majority of the cannabidiol of the second fractionated aqueous phase comprises combining the second fractionated aqueous phase and a second solubility-regulating composition to (i) drive a portion of the cannabidiol of the second fractionated aqueous phase out of the second fractionated aqueous phase and (ii) produce a second heterogeneous composition, in which:

the second solubility-regulating composition comprises a Brønsted acid;

the second heterogeneous composition comprises (a) substantially all of the ethanol of the second fractionated aqueous phase, (b) substantially all of the cannabidiol of the second fractionated aqueous phase, and (c) substantially all of the water of the second fractionated aqueous phase;

the second heterogeneous composition comprises a residual aqueous phase and a cannabidiol-enriched lipid phase;

the residual aqueous phase is a liquid;

the residual aqueous phase comprises greater than 50 percent of the ethanol of the second heterogeneous composition;

the residual aqueous phase comprises greater than 95 percent of the water of the second heterogeneous composition;

the cannabidiol of the second heterogeneous composition comprises molecular cannabidiol;

the Brønsted acid of the second solubility-regulating composition converts a majority of the ionic cannabidiol of the second fractionated aqueous phase into molecular cannabidiol;

the molecular cannabidiol of the second heterogeneous composition has a solubility in the residual aqueous phase that is less than 10 grams per liter;

the cannabidiol-enriched lipid phase comprises greater than 80 percent of the molecular cannabidiol of the second heterogeneous composition;

the separation of (a) the majority of the ethanol of the second fractionated aqueous phase and the majority of the water of the second fractionated aqueous phase from (b) the majority of the cannabidiol of the second fractionated aqueous phase further comprises mechanically separating the residual aqueous phase of the second heterogeneous composition from the cannabidiol-enriched lipid phase of the second heterogeneous composition; and the product consists essentially of the portion of the cannabidiol-enriched lipid phase that is mechanically separated from the residual aqueous phase.

12. The method of claim 1, in which:

the separation of (a) the majority of the ethanol of the second fractionated aqueous phase and the majority of the water of the second fractionated aqueous phase from (b) the majority of the cannabidiol of the second fractionated aqueous phase comprises (i) vaporizing the majority of the ethanol of the second fractionated aqueous phase to produce ethanol vapor, (ii) vaporizing the majority of the water of the second fractionated aqueous phase to produce water vapor, and (iii) removing both the ethanol vapor and the water vapor from the second fractionated aqueous phase using a vacuum;

the vaporizing and removing are performed under conditions that do not vaporize and remove the majority of the cannabidiol of the second fractionated aqueous phase from the second fractionated aqueous phase; and the product consists of the portion of the second fractionated aqueous phase that is not both vaporized and removed from the second fractionated aqueous phase.

13. The method of claim 1, in which:

the separation of (a) the majority of the ethanol of the second fractionated aqueous phase and the majority of the water of the second fractionated aqueous phase from (b) the majority of the cannabidiol of the second fractionated aqueous phase comprises combining the second fractionated aqueous phase and a second solubility-regulating composition to (i) drive a portion of the cannabidiol of the second fractionated aqueous phase out of the second fractionated aqueous phase and (ii) produce a second heterogeneous composition, in which:

the second solubility-regulating composition comprises water at a concentration by mass that is greater than the concentration by mass of the water that is present in the second fractionated aqueous phase such that the combination of the second fractionated aqueous phase and the second solubility-regulating composition has a greater concentration of water than the second fractionated aqueous phase;

the second heterogeneous composition comprises (a) substantially all of the ethanol of the second fractionated aqueous phase, (b) substantially all of the cannabidiol of the second fractionated aqueous phase, (c) substantially all of the water of the second fractionated aqueous phase, and (d) the water of the second solubility-regulating composition;

the second heterogeneous composition comprises a residual aqueous phase and a cannabidiol-enriched lipid phase;

the residual aqueous phase is a liquid;

the residual aqueous phase comprises greater than 50 percent of the ethanol of the second heterogeneous composition;

the residual aqueous phase comprises greater than 95 percent of the water of the second heterogeneous composition;

the cannabidiol of the second heterogeneous composition has a solubility in the residual aqueous phase that is less than 10 grams per liter;

the cannabidiol-enriched lipid phase comprises greater than 80 percent of the cannabidiol of the second heterogeneous composition;

the cannabidiol-enriched lipid phase comprises the cannabidiol of the cannabidiol-enriched lipid phase and any tetrahydrocannabinol that is present in the cannabidiol-enriched lipid phase at a cannabidiol-to-tetrahydrocannabinol ratio that is greater than 350:1 by mass;

the separation of (a) the majority of the ethanol of the second fractionated aqueous phase and the majority of the water of the second fractionated aqueous phase from (b) the majority of the cannabidiol of the second fractionated aqueous phase further comprises mechanically separating the residual aqueous phase of the second heterogeneous composition from the cannabidiol-enriched lipid phase of the second heterogeneous composition; and the product consists essentially of the portion of the cannabidiol-enriched lipid phase that is mechanically separated from the residual aqueous phase.

14. The method of claim 13, in which the mechanical separation of the residual aqueous phase of the second heterogeneous composition from the cannabidiol-enriched lipid phase of the second heterogeneous composition comprises centrifuging the second heterogeneous composition to produce (a) an aqueous liquid, which comprises the majority of the ethanol of the second fractionated aqueous phase and the majority of the water of the second fractionated aqueous phase, and (b) an oil and any precipitate, which both comprises the majority of the cannabidiol of the second fractionated aqueous phase and is the product.

15. The method of claim 1, in which:

the alcohol phase of the starting composition has an ionic strength that is less than 100 millimolar;

the aqueous phase of the heterogeneous composition has an ionic strength that is greater than 100 millimolar;

the ionic strength of the aqueous phase of the heterogeneous composition is at least 10 times greater than the ionic strength of the alcohol phase of the starting composition; and decreasing the solubility of the tetrahydrocannabinol in the alcohol phase comprises increasing the ionic strength of the alcohol phase by combining the alcohol phase with the solubility-regulating composition.

16. The method of claim 1, in which:

the separation of (a) the majority of the ethanol of the second fractionated aqueous phase and the majority of the water of the second fractionated aqueous phase from (b) the majority of the cannabidiol of the second fractionated aqueous phase comprises combining the second fractionated aqueous phase and a second solubility-regulating composition to (i) drive a portion of the cannabidiol of the second fractionated aqueous phase out of the second fractionated aqueous phase and (ii) produce a second heterogeneous composition;

the second heterogeneous composition comprises (a) substantially all of the ethanol of the second fractionated aqueous phase, (b) substantially all of the cannabidiol of the second fractionated aqueous phase, and (c) substantially all of the water of the second fractionated aqueous phase;

the alcohol phase has an ionic strength of at least 0.25 micromolar and no greater than 100 millimolar;

the aqueous phase of the heterogeneous composition has an ionic strength that is no greater than 100 millimolar;

the second fractionated aqueous phase has an ionic strength that is no greater than 100 millimolar;

the second heterogeneous composition comprises a residual aqueous phase and a cannabidiol-enriched lipid phase;

the residual aqueous phase of the second heterogeneous composition has an ionic strength of at least 100 millimolar;

the ionic strength of the residual aqueous phase of the second heterogeneous composition is at least 10 times greater than the ionic strength of the aqueous phase of the heterogeneous composition;

the residual aqueous phase is a liquid;

the residual aqueous phase comprises greater than 50 percent of the ethanol of the second heterogeneous composition;

the residual aqueous phase comprises greater than 95 percent of the water of the second heterogeneous composition;

the cannabidiol of the second heterogeneous composition has a solubility in the residual aqueous phase that is less than 10 grams per liter;

the cannabidiol-enriched lipid phase comprises greater than 80 percent of the cannabidiol of the second heterogeneous composition;

the cannabidiol-enriched lipid phase comprises the cannabidiol of the cannabidiol-enriched lipid phase and any tetrahydrocannabinol that is present in the cannabidiol-enriched lipid phase at a cannabidiol-to-tetrahydrocannabinol ratio that is greater than 350:1 by mass;

the separation of (a) the majority of the ethanol of the second fractionated aqueous phase and the majority of the water of the second fractionated aqueous phase from (b) the majority of the cannabidiol of the second fractionated aqueous phase further comprises mechanically separating the residual aqueous phase of the second heterogeneous composition from the cannabidiol-enriched lipid phase of the second heterogeneous composition; and the product consists essentially of the portion of the cannabidiol-enriched lipid phase that is mechanically separated from the residual aqueous phase.

17. The method of claim 1, in which:

the starting composition has a temperature of at least 20 degrees Celsius and no greater than 65 degrees Celsius; and the product is produced at a temperature of at least 20 degrees Celsius and no greater than 65 degrees Celsius.

18. The method of claim 12, in which:

the product is produced at a temperature that is less than the freezing point of cannabidiol;

the product comprises a glass;

the glass comprises greater than 50 percent of the cannabidiol of the product;

the glass comprises cannabidiol at a concentration greater than 50 percent by mass;

the glass has a glass-transition temperature that is less than the freezing point of cannabidiol;

the glass lacks a freezing point; and the glass lacks a melting point.

19. The method of claim 16, in which:

the product is produced at a temperature that is less than the freezing point of cannabidiol;

the product comprises crystals;

the crystals comprise greater than 50 percent of the cannabidiol of the product;

the crystals comprise cannabidiol at a concentration greater than 50 percent by mass;

the crystals have a melting point; and the crystals lack a glass-transition temperature.

20. The method of claim 17, in which:

the product is produced at a temperature that is less than the freezing point of cannabidiol;

the product comprises an oil;

the oil comprises greater than 50 percent of the cannabidiol of the product;

the oil comprises cannabidiol at a concentration greater than 50 percent by mass;

the oil is a supercooled liquid;

the oil has a freezing point; and the oil lacks a glass-transition temperature.

* * * * *